United States Patent
Wordham et al.

(10) Patent No.: US 10,231,669 B2
(45) Date of Patent: *Mar. 19, 2019

(54) EQUINE PERFORMANCE TRACKING AND MONITORING SYSTEM

(71) Applicant: Hylonome LLC, Norwalk, CT (US)

(72) Inventors: Laxmi Stebbins Wordham, Larchmont, NY (US); Katharine McGuinn Motley, Rowayton, CT (US); Eliane Cordia van Reesema, Rowayton, CT (US); Cornelis Josephus van Beckhoven, Haghorst (NL)

(73) Assignee: Hylonome LLC, Norwalk, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/010,676

(22) Filed: Jun. 18, 2018

(65) Prior Publication Data

US 2018/0303425 A1    Oct. 25, 2018

Related U.S. Application Data

(63) Continuation of application No. 15/721,187, filed on Sep. 29, 2017, now Pat. No. 9,999,392.

(Continued)

(51) Int. Cl.
*A61B 5/00* (2006.01)
*A61B 5/0205* (2006.01)
(Continued)

(52) U.S. Cl.
CPC .......... *A61B 5/6831* (2013.01); *A61B 5/0006* (2013.01); *A61B 5/0205* (2013.01);
(Continued)

(58) Field of Classification Search
CPC . A61B 5/0006; A61B 5/0205; A61B 5/02405; A61B 5/02438; A61B 5/0245;
(Continued)

(56) References Cited

U.S. PATENT DOCUMENTS

| | | | |
|---|---|---|---|
| 9,999,392 B1* | 6/2018 | Wordham | A61B 5/6831 |
| 2006/0173367 A1* | 8/2006 | Stuart | A01K 13/008 |
| | | | 600/508 |
| 2007/0130893 A1* | 6/2007 | Davies | A01K 11/008 |
| | | | 54/1 |
| 2010/0045463 A1* | 2/2010 | Bradley | A01K 11/008 |
| | | | 340/573.1 |
| 2016/0100802 A1* | 4/2016 | Newman | G06F 19/3418 |
| | | | 600/301 |

OTHER PUBLICATIONS

Arioneo, "Orscana", hardware/software for measuring vitals at rest, retrieved Nov. 6, 2017, product was commercially available and could be located at https://www.arioneo.com/en/home/care/.

(Continued)

*Primary Examiner* — Michael J Carey
(74) *Attorney, Agent, or Firm* — Kolitch Romano LLP

(57) ABSTRACT

An equine performance tracking and monitoring system having real-time feedback may include a horse heart rate monitoring strap configured to be secured against a portion of a horse while extending only part of the way around the horse. To measure the horse's heart rate, the disclosed systems may utilize such a discrete-length horse heart rate monitoring strap having electrodes, one of which is positioned behind the left elbow of the horse. The horse's heart rate may be transmitted to a wearable device work by a rider. The wearable device may include a sensor configured to measure the heart rate of the rider. The heart rate of the horse and the heart rate of the rider may each be presented to the rider, for example, via a display of the wearable device.

21 Claims, 13 Drawing Sheets

Related U.S. Application Data

(60) Provisional application No. 62/448,653, filed on Jan. 20, 2017.

(51) Int. Cl.
*A61B 5/0404* (2006.01)
*A61B 5/0408* (2006.01)
*A61B 5/044* (2006.01)
*A61B 5/0245* (2006.01)
*A61B 5/024* (2006.01)
*A61B 5/11* (2006.01)

(52) U.S. Cl.
CPC ........ *A61B 5/0245* (2013.01); *A61B 5/02438* (2013.01); *A61B 5/044* (2013.01); *A61B 5/0404* (2013.01); *A61B 5/04085* (2013.01); *A61B 5/11* (2013.01); *A61B 5/6823* (2013.01); *A61B 5/7475* (2013.01); *A61B 5/02405* (2013.01); *A61B 5/112* (2013.01); *A61B 5/1118* (2013.01); *A61B 5/1123* (2013.01); *A61B 2503/40* (2013.01); *A61B 2562/0219* (2013.01)

(58) Field of Classification Search
CPC ... A61B 5/0404; A61B 5/04085; A61B 5/044; A61B 5/11; A61B 5/6823; A61B 5/6831; A61B 5/7475; A61B 2503/40; A61B 2562/0219
USPC .................................................. 600/300, 301
See application file for complete search history.

(56) References Cited

OTHER PUBLICATIONS

Equestic Holdings BV, "Equestic", hardware/software for performance tracking, retrieved Nov. 6, 2017, product was commercially available and could be located at https://www.equestic.com/?lang=en.

Equisense, "Equisense Motion", hardware/software for performance tracking/gait analysis, retrieved Nov. 6, 2017, product was commercially available and could be located at https://equisense.com/en.

E-TRAKKA, "E-TRAKKA® Equine Fitness Monitoring", hardware/software for performance tracking, retrieved Nov. 6, 2017, product was commercially available and could be located at http://www.etrakka.com/au/.

Fine Equity, "equinITy Intelligent Training", hardware software for performance tracking, retrieved Nov. 6, 2017, product was commercially available and could be located at http://www.fineequity.com/.

KER Clockit, "KER ClockIt™", software for performance tracking, retrieved Nov. 6, 2017, product was commercially available and could be located at http://www.kerclockit.com/sport/.

Nightwatch, "Nightwatch® Equine Distress & Wellness Monitor", hardware/software for measuring vitals at rest, retrieved Nov. 6, 2017, product was commercially available and could be located at http://www.nightwatch24.com/™welcome-folio.

Polar®, "Equine H7 heart rate sensor electrode base set", hardware/software for performance tracking with heart rate, retrieved Nov. 6, 2017, product was commercially available and could be located at https://www.polar.com/us-en/products/equine/accessories/equine_H7_heart_rate_sensor_electrode_base_set.

Polar®, "Polar Sport Zones for Horses", hardware/software for performance tracking with heart rate, retrieved Nov. 6, 2017, product was commercially available and could be located at https://www.polar.com/us-en/prodcuts/equine/why_measure_your_horses_heart_rate/polar_sport_zones_for_horses.

Seehorse, "SeeHorse", hardware/software for measuring vitals at rest, retrieved Nov. 6, 2017, product was commercially available and could be located at http://seehorse.ca/.

U.S. Patent and Trademark Office, Office action in U.S. Appl. No. 15/721,187, dated Feb. 28, 2018, which is another application of Applicant Hylonome LLC that shares the same priority as this U.S. application.

U.S. Receiving Office, International Search Report and Written Opinion of the International Searching Authority in PCT/US2018/014544, dated May 29, 2018, which is an international application of Applicant Hylonome LLC that shares the same priority as this U.S. application.

\* cited by examiner

EQUINE PERFORMANCE TRACKING AND MONITORING SYSTEM

FIELD

This disclosure relates to systems and methods for tracking and monitoring equine performance and fitness. More specifically, the disclosed embodiments relate to an animal-mounted system for tracking and monitoring heart rate and other aspects of an animal's athletic performance.

INTRODUCTION

Horses are tremendous athletes, but they cannot communicate everything to their riders. Wearable technologies for humans allow human athletes to know everything about their own training sessions: speed, steps, acceleration, hydration, muscle recovery etc. However, the same is not true of equine athletes. There is no in-ride feedback that allows riders to alter the way they train or ride and ensure they are promoting the overall health and wellbeing of their horses. Riders are left to guess the appropriate level of training for each of their horses. Among other shortcomings, known solutions fail to provide in-the-moment feedback to the rider, and also fail to provide in-depth analysis of training sessions after the fact.

SUMMARY

The present disclosure provides systems, apparatuses, and methods relating to an equine performance tracking and monitoring system having real-time feedback. In some embodiments, an equine performance tracking and monitoring system may include: an elongate heart rate (HR) monitoring strap having a first electrode at a first end portion and a second electrode at a second end portion, the first and second electrodes being electrically coupled to a transmitter; one or more flaps, each extending outward from a long edge of the elongate HR monitoring strap, wherein the HR monitoring strap is configured to attach to a horse by sandwiching the strap between a body of the horse and a girth portion of a saddle on the horse with the one or more flaps releasably fastened around the girth portion of the saddle, such that the heart rate monitoring strap is against the body of the horse and extends only partially around the body of the horse, and wherein the first and second electrodes monitor a heart rate of the horse; and a wearable electronic device, wearable by a rider of the horse, having a display screen and configured to receive heart rate signals from the transmitter of the HR monitoring strap; wherein a processor of the wearable electronic device is configured to execute a set of stored instructions to determine a heart rate zone, selected from a plurality of defined heart rate zones, corresponding to a currently measured heart rate of the horse, and to cause the display screen to present, in real time, an indicator corresponding to the determined heart rate zone.

In some embodiments, a system for measuring physical characteristics of a horse may include: a heart rate (HR) monitoring strap configured to fit between a horse and a girth portion of a saddle on the horse, wherein the strap includes at least two spaced-apart electrodes and has a length configured to be shorter than a circumference of a body of the horse, such that the strap extends only partially around the body of the horse when installed; one or more flaps, each extending laterally from a long edge of the strap, the one or more flaps being configured to fasten around the girth portion of the saddle, thereby securing the strap relative to the girth portion of the saddle; a wearable electronic device, wearable by a rider of the horse and configured to receive wireless communications; a transmitter coupled to the HR monitoring strap and in electrical communication with the at least two electrodes, the transmitter configured to transmit horse heart rate information wirelessly to the wearable electronic device; and a computer application of the wearable electronic device configured to process the horse heart rate information from the transmitter and display the processed horse heart rate information on a screen of the wearable electronic device.

In some embodiments, a method for monitoring a heart rate of a horse over the course of a plurality of rides may include: installing a noncircumferential horse heart rate monitoring (HRM) strap on a horse by: placing a saddle on the horse; after placing the saddle on the horse, disposing the horse HRM strap on an exterior surface of the horse such that an upper end of the horse HRM strap is under a saddle pad of the saddle and a lower end of the horse HRM strap is disposed behind a left elbow of the horse; and securing the horse HRM strap in place by fastening one or more flaps, each extending from a respective lateral side of the horse HRM strap, around a girth portion of the saddle; and using a heart rate monitoring system to measure a heart rate of the horse using the noncircumferential horse HRM strap during each ride of a plurality of rides; wherein the heart rate monitoring system is configured to determine and display characteristics of each of the plurality of rides on a screen display of an electronic device, and the characteristics of each of the plurality of rides include the heart rate of the horse.

Features, functions, and advantages may be achieved independently in various embodiments of the present disclosure, or may be combined in yet other embodiments, further details of which can be seen with reference to the following description and drawings.

DESCRIPTION

Figure 1:
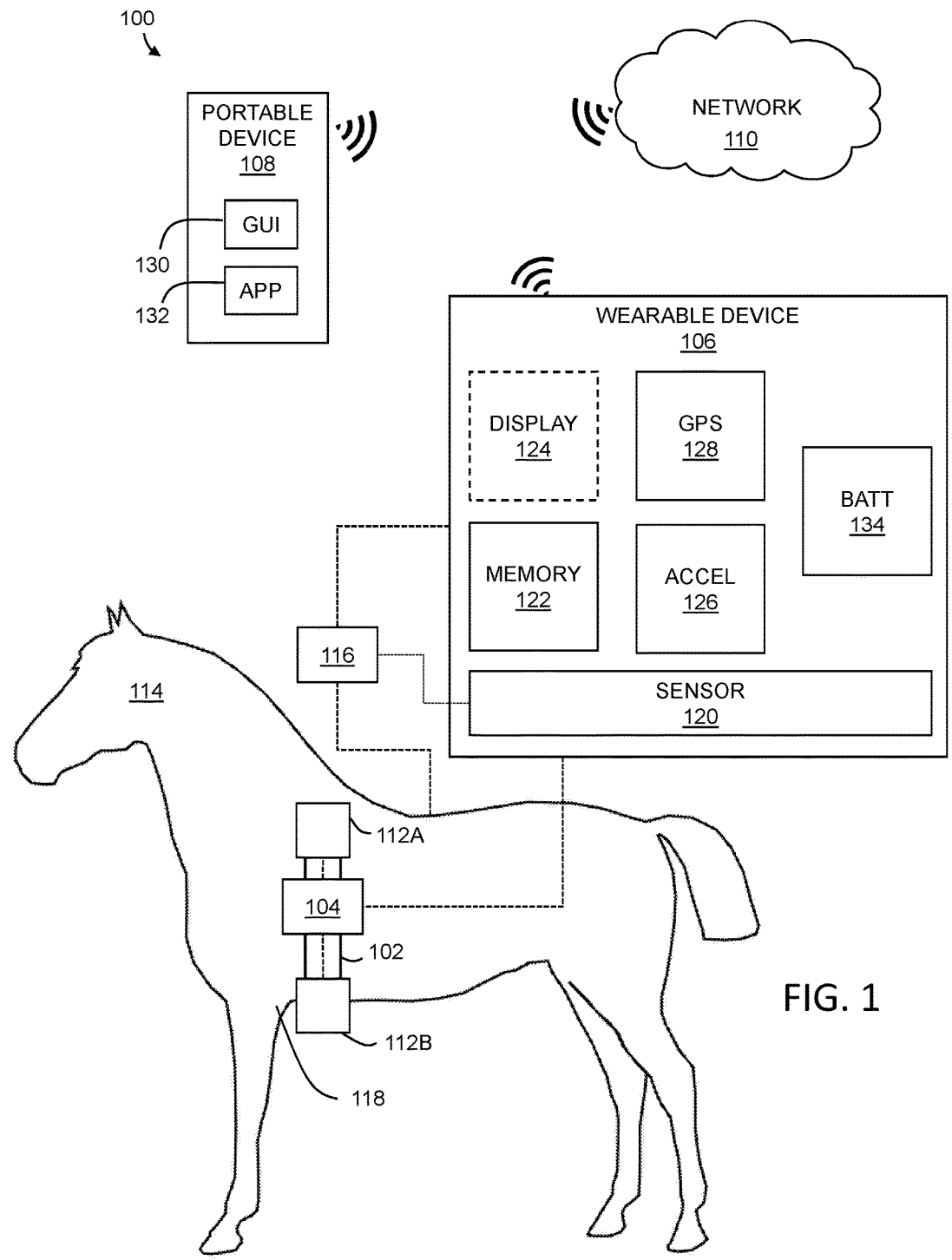
FIG. 1 is a schematic diagram of an illustrative equine performance tracking and monitoring system having real-time feedback.

Various aspects and examples of an equine performance tracking and monitoring system having real-time feedback, as well as related methods, are described below and illustrated in the associated drawings. Unless otherwise specified, an equine performance tracking and monitoring system and/or its various components may, but are not required to, contain at least one of the structures, components, functionalities, and/or variations described, illustrated, and/or incorporated herein. Furthermore, unless specifically excluded, the process steps, structures, components, functionalities, and/or variations described, illustrated, and/or incorporated herein in connection with the present teachings may be included in other similar devices and methods, including being interchangeable between disclosed embodiments. The following description of various examples is merely illustrative in nature and is in no way intended to limit the disclosure, its application, or uses. Additionally, the advantages provided by the examples and embodiments described below are illustrative in nature and not all examples and embodiments provide the same advantages or the same degree of advantages.

Definitions

The following definitions apply herein, unless otherwise indicated.

"Substantially" means to be more-or-less conforming to the particular dimension, range, shape, concept, or other aspect modified by the term, such that a feature or component need not conform exactly. For example, a "substantially cylindrical" object means that the object resembles a cylinder, but may have one or more deviations from a true cylinder.

"Comprising," "including," and "having" (and conjugations thereof) are used interchangeably to mean including but not necessarily limited to, and are open-ended terms not intended to exclude additional, unrecited elements or method steps.

Terms such as "first", "second", and "third" are used to distinguish or identify various members of a group, or the like, and are not intended to show serial or numerical limitation.

"Coupled" means connected, either permanently or releasably, whether directly or indirectly through intervening components, and is not necessarily limited to physical connection(s).

Directional terms such as "inboard," "outboard," "left," "right," "front," "rear," and the like are intended to be understood in the context of a host animal (e.g., a horse) on which systems described herein may be mounted or otherwise attached. For example, "outboard" may indicate a relative position that is laterally farther from the centerline of the animal, or a direction that is away from the animal's centerline. Conversely, "inboard" may indicate a direction toward the centerline, or a relative position that is closer to the centerline. "Left" indicates the left-hand portion of the animal (e.g. from the perspective of a rider), while "right" indicates a right-hand portion of the animal (e.g. from the perspective of a rider). Similarly, "forward" means toward the front portion (e.g., the head) of the animal, and "rear" means toward the rear of the animal. In the absence of a host animal, the same directional terms may be used as if the animal were present. For example, even when viewed in isolation, a component may have a "forward" edge, based on the fact that the edge in question would be installed facing the head of a host animal.

Overview

Heart rate is a great indicator of wellness and overall wellbeing for horses, and can be monitored both during training and when a horse is at rest. Heart rate monitoring benefits include facilitation of: tracking of fitness variability, adjustment of training rigor, and early detection of injury/illness. Equine performance tracking and monitoring systems described herein offer high-accuracy heart rate monitoring having real-time, in-ride feedback to the rider, such that training adjustments can be made from the saddle. The disclosed equine performance tracking and monitoring systems also combine heart rate during training with geographical path data to give improved insights to riders and trainers. In some examples, additional measurements may be incorporated, such as speed, distance traveled, hydration, muscle recovery, calories burned, respiration, temperature, humidity, altitude etc.

The disclosed equine performance tracking and monitoring system helps trainers and owners improve the overall health and fitness of their horses through measurable data. The device measures and analyzes several key components of performance including the heart rate of the horse, the heart rate of the rider, their movements, and external variables that might impact a training session. FIG. 1 shows a schematic diagram of an illustrative equine performance tracking and monitoring system generally indicated at 100.

In general, an equine performance tracking and monitoring system having real-time feedback, such as system 100, may include a heart rate monitoring strap 102, a transmitter 104 coupled to heart rate strap 102, a wearable electronic device 106, and a portable electronic device 108. Wearable device 106 may be configured to pair with one or more portable electronic devices 108 during and/or after a training session. Different components of the system may be connected by and/or information may be stored in a computer network 110, such as a local area network (LAN) and/or the Internet. Computer network 110 is described in more detail below, and may be referred to as the "cloud." Furthermore, wearable device 106 and electronic devices 108 comprise examples of data processing systems, which are also described in more detail below.

Heart rate monitoring strap 102 and/or wearable device 106 may include any suitable circuits, modules, software, and/or devices configured to monitor activity and biometric information of horse 114, and to provide real-time visual feedback to a rider 116 of the horse. Activity and biometric information relating to rider 116 may also be collected and displayed. For example, heart rate monitoring strap 102 includes electrodes 112A and 112B, and is configured to be positioned at least partially behind a left elbow 118 of horse 114 to measure the horse's heart rate (e.g., average or running average in real time). In some examples, the horse's heart rate may be measured every second. In some examples, electrodes 112A and 112B may be configured to detect, when placed against the exterior of the animal, electrical signals corresponding to heart rate. The heart rate is then transmitted by a transmitter 104 or other suitable device to wearable device 106 on rider 116. Wearable device 106 may include any suitable electronic device configured to be worn by a rider, for example a smart watch, and may include sensor(s) 120 (e.g., optical sensors) configured to track and report the heart rate of rider 116 (e.g., average or running average in real time) in tandem with the horse's heart rate. The heart rates of horse 114 and of rider 116 may each be compared to known, respective "training heart rate zones" and stored in memory 122.

In some examples, sensors 120 may include electrodes disposed on a chest strap or other device worn by rider 116, and may transmit heart rate information regarding rider 116 to wearable device 106 (or portable electronic device 108) via a Bluetooth® wireless technology standard, Bluetooth® LE wireless technology standard, radio, and/or WiFi wireless technology standard, and/or other suitable wireless and/or wired connection. In some examples, portable device 108 and wearable device 106 may be the same device, for example a smart phone or tablet; in this case, portable electronic device 108 may be carried by the rider during training sessions to facilitate acquiring GPS and/or accelerometer data of the ride.

Electrodes 112A, 112B may include any suitable sensors configured to detect signals (e.g., electrical or optical signals) corresponding to the heart rate of animal 114. Electrodes 112A, 112B are in electrical communication with transmitter 104, which transmits the information from the pair of electrodes to wearable device 106. Wearable device 106, stores the information in memory 122. In some examples, electrodes 112A, 112B may include a conductive fabric comprising silver or other conductive material. In some examples, electrodes 112A, 112B may be electrically coupled to transmitter 104 by respective conductive members, e.g., comprising conductive rubber. In some examples, electrodes 112A, 112B are coupled to transmitter 104 by wires or leads. In some examples, electrodes 112A, 112B are coupled to transmitter 104 wirelessly. In some examples, electrodes 112A, 112B are coupled directly to transmitter 104. In some examples, electrodes 112A, 112B may include one or more optical sensors.

In some examples, sensors 120 may be integrated with wearable device 106 which stores the heart rate information from sensors 120 in memory 122. In some examples, sensors 120 may include one or more optical sensors (e.g. for detecting blood flow through the rider's wrist). In some examples, sensors 120 may include electrodes configured to detect, when placed against the rider's skin, electrical signals corresponding to heart rate. In some examples, sensors 120 may be located on a chest strap worn by the rider, in which case wearable device 106 and portable electronic device 108 may be the same device and portable electronic device 108 may be carried by the rider during the training session.

Wearable device 106 may be configured to be used to start and/or stop a training session and/or to start/stop the recording of heart rate information for both horse and rider. A visual indication of the heart rate of the horse may be displayed to the rider, for example, via a display 124 of wearable device 106. A visual indication of the heart rate of the rider may also be displayed to the rider, for example, via display 124 of wearable device 106. Wearable device 106 may be configured to store the ride data (i.e. heart rate information for both the horse and the rider, as well as any other measurements made during the ride). This ride data may be stored in memory 122 during the ride and transmitted to portable electronic device 108 after the ride.

Indication of the heart rate of the horse and/or the rider by display 124 may include indicating a particular "heart rate zone" into which the heart rate falls. For example, an equine heart rate may be divided into a plurality of zones (e.g., five zones), based on expert opinion, training level, assessment, discipline, and the like. Wearable device 106 may be configured to provide a visual indication of the heart rate zone for horse 114, in real time. For example, wearable device 106 may include a display 124 configured to present an indicator, a display element, or a graphic having a respective color associated with each zone (or a subset of the zones). In some examples, a portion of display 124 may turn green when the heart rate is determined to be in a desired training zone, red when the heart rate is in an undesired zone, and/or blue when the heart rate is in a zone between the two. Each zone may have a unique color and/or some zones may be grouped. In some examples, display 124 may comprise a graphical user interface. Display 124 may include textual information, such as present heart rate, and/or may have a background color corresponding to the present heart rate zone. In general, display 124 may include any suitable display or indicator (e.g., visual) configured to quickly, intuitively, and unambiguously communicate a present heart rate zone of the horse and the rider to rider 116. In some examples, display 124 may include an audible component, such as a tone produced via speaker or earphone.

Transmission of the heart rate information from transmitter 104 to wearable device 106 may occur via a wireless or physical connection, a Bluetooth connection such as a Bluetooth® Low Energy wireless technology standard (BLE) connection, an internet connection, a radio connection, and/or any other suitable communication method. Transmission of heart rate information from transmitter 104 to wearable electronic device 106 may occur in real time during the ride. Transmission of ride data from wearable electronic device 106 to portable electronic device 108 may occur after ride completion, for example, when the devices are synced. Transmission of ride data from wearable device 106 to portable electronic device 108 may occur via a wireless connection such as a Bluetooth® connection, a BLE connection, an internet connection, a radio connection, and/or any other suitable communication method. In some examples, wearable device 106 and portable electronic device 108 are the same device. In some examples, wearable device 106 and/or portable device 108 may comprise a smart phone, personal computer, laptop, tablet, and/or remote server.

The disclosed equine performance tracking and monitoring systems may also measure movement, using an accelerometer circuit 126 having one or more accelerometers (e.g., one or more three-axis accelerometers) and/or a global positioning system (GPS) module 128 onboard wearable device 106. Such movement data may be stored in memory 122, and may be transmitted with the stored heart rate information for both the horse and the rider to portable electronic device 108 and/or network 110 (e.g., to a server) after the ride (e.g. when the devices are next synced). Movement data related to horse 114 may be analyzed to assess various aspects over time, such as gait, left/right lead, transitions between activities, and/or the like, or any combination of these. Movement information may be compared against heart rate information, expected values, same-animal history, group data, etc. Additional description of such processing can be found below, with respect to method 300.

GPS module 128 may include any suitable GPS receiver configured to provide geographical location information. Such information may be obtained continuously or periodically, and/or GPS module 128 may be inactive when wearable device 106 is disabled. GPS information may be stored in memory 122 for later retrieval. For example, a training session may be plotted on a displayed map (e.g., on wearable device 106 or on portable electronic device 108), in real time and/or after the fact. In some examples, portable electronic device 108 may be carried by the rider during the training session and the movement data may be acquired by an accelerometer and/or onboard GPS located on portable electronic device 108.

Figure 4:
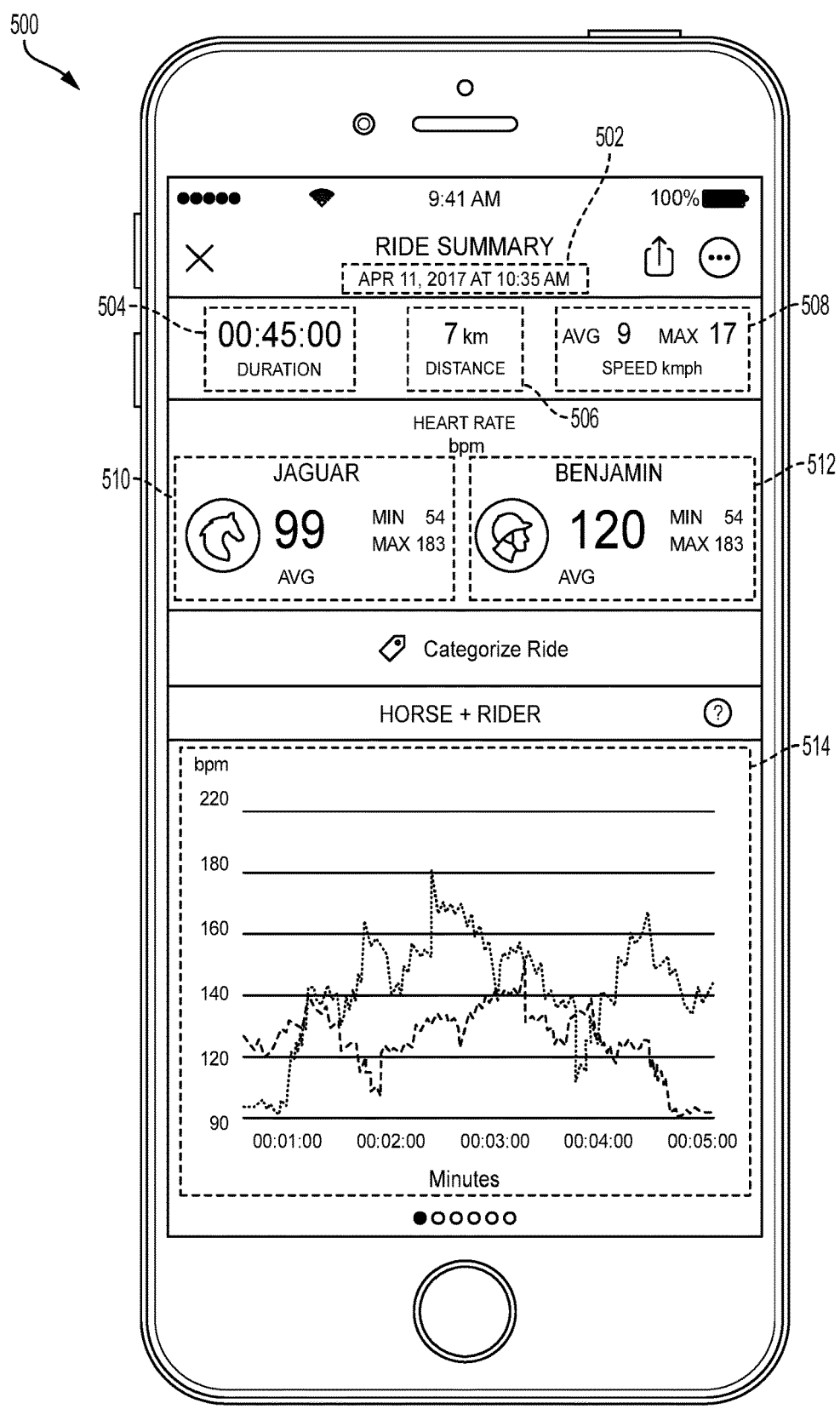
FIG. 4 is a schematic diagram of an embodiment of a graphical user interface suitable for use with the present disclosure.

Portable electronic device 108 may include any suitable device having an onboard computer and wireless communication capabilities, such as a smartphone or tablet. Portable electronic device 108 may comprise a data processing system (see Section D below) having a graphical user interface (GUI) 130 and running a software application (app) 132. App 132 may be part of system 100, and may be configured to collate and display information regarding horse 114, e.g., for one or more training sessions, on GUI 130. For example, graphs of heart rate, speed, and/or gait vs. time may be displayed in the app, as well as distance and/or geographical route information. Heart rate information of rider 116 may be displayed with the horse information, for enhanced analysis. An illustrative example of GUI 130 is shown in FIG. 4 and discussed further below.

In some examples, transmission of ride data (i.e. heart rate and/or movement data) from portable electronic device 108 to network 110 may happen simultaneously during the ride. Network 110 may comprise processing and/or data storage functionality with respect to system 100. For example, ride data may be stored in the cloud (e.g. network 110) for further sharing, display, and analysis, and a service associated with the disclosed system may provide insights and advice to riders. In some examples, app 132 may be used to access horse-related training information from other users of similar systems. For example, a user may compare a specific horse's training performance against that of a general population of horses having similar characteristics. In some examples, the data relating to other horses in the population may be stored and accessed via network 110. In some examples, various aspects of analysis having to do with machine learning or artificial intelligence may be executed over network 110. Transmission of ride data to network 110 may occur simultaneously during the ride, and/or may occur after the ride when wearable device 106 and portable electronic device 108 are next synced, and/or at any time thereafter.

Components of wearable device 106 may be powered by an onboard battery 134, which may include any suitable portable power supply, such as a battery, a rechargeable battery, an ultracapacitor, a fuel cell, and/or the like, or any combination of these. In some examples, battery 134 may include a Lithium Ion battery. In some examples, battery 134 may include a Lithium Polymer (LiPo) battery.

To provide ride analysis, system 100 may perform analyses on, and in some cases apply machine learning to, the recorded movement and heart rate data, thereby determining the type of movement and exercises performed, the duration of those exercises, and the horse's exertion level and recovery patterns during the ride. That analysis is then used to generate written and/or visual advice and analysis summaries. System 100 may allow riders to view previous sessions, and/or share that data with anyone they choose, both in real time (as they ride) and for previous sessions. System 100 may allow a rider to compare a training session against past training sessions for the same horse and/or against training sessions of other horses. It may also allow trainers and horse owners to view and filter data, e.g., on a per-horse basis. System 100 may also contain a dataset of expert-collected horse training data, for use as a basis for its recommendations and analysis and/or as a comparison against other horses in the system.

Aspects of the equine performance tracking and monitoring systems of the present disclosure, and/or related methods, may be embodied as a computer method, computer system, or computer program product. Accordingly, aspects of the equine performance tracking and monitoring system may take the form of an entirely hardware embodiment, an entirely software embodiment (including firmware, resident software, micro-code, and the like), or an embodiment combining software and hardware aspects, all of which may generally be referred to herein as a "circuit," "module," or "system." Furthermore, aspects of the equine performance tracking and monitoring system may take the form of a computer program product embodied in a computer-readable medium (or media) having computer-readable program code/instructions embodied thereon.

Any combination of computer-readable media may be utilized. Computer-readable media can be a computer-readable signal medium and/or a computer-readable storage medium. A computer-readable storage medium may include an electronic, magnetic, optical, electromagnetic, infrared, and/or semiconductor system, apparatus, or device, or any suitable combination of these. More specific examples of a computer-readable storage medium may include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, and/or any suitable combination of these and/or the like. In the context of this disclosure, a computer-readable storage medium may include any suitable tangible medium that can contain or store a program for use by or in connection with an instruction execution system, apparatus, or device.

A computer-readable signal medium may include a propagated data signal with computer-readable program code embodied therein, for example, in baseband or as part of a carrier wave. Such a propagated signal may take any of a variety of forms, including, but not limited to, electromagnetic, optical, and/or any suitable combination thereof. A computer-readable signal medium may include any computer-readable medium that is not a computer-readable storage medium and that is capable of communicating, propagating, or transporting a program for use by or in connection with an instruction execution system, apparatus, or device.

Program code embodied on a computer-readable medium may be transmitted using any appropriate medium, including but not limited to wireless, wireline, optical fiber cable, RF, and/or the like, and/or any suitable combination of these.

Computer program code for carrying out operations for aspects of the equine performance tracking and monitoring system may be written in one or any combination of programming languages, including an object-oriented programming language such as the Java language, C++, and/or the like, and conventional procedural programming languages, such as C. Mobile apps may be developed using any suitable language, including those previously mentioned, as well as Objective-C, Swift, C#, HTML5, and the like. The program code may execute entirely on a user's computer, partly on the user's computer, as a stand-alone software package, partly on the user's computer and partly on a remote computer, or entirely on the remote computer or server. In the latter scenario, the remote computer may be connected to the user's computer through any type of network, including a local area network (LAN) or a wide area network (WAN), and/or the connection may be made to an external computer (for example, through the Internet using an Internet Service Provider).

Aspects of the equine performance tracking and monitoring system are described below with reference to flowchart illustrations and/or block diagrams of methods, apparatuses, systems, and/or computer program products. Each block and/or combination of blocks in a flowchart and/or block diagram may be implemented by computer program instructions. The computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions can also be stored in a computer-readable medium that can direct a computer, other programmable data processing apparatus, and/or other device to function in a particular manner, such that the instructions stored in the computer-readable medium produce an article of manufacture including instructions which implement the function/act specified in the flowchart and/or block diagram block or blocks.

The computer program instructions can also be loaded onto a computer, other programmable data processing apparatus, and/or other device to cause a series of operational steps to be performed on the device to produce a computer-implemented process such that the instructions which execute on the computer or other programmable apparatus provide processes for implementing the functions/acts specified in the flowchart and/or block diagram block or blocks.

Any flowchart and/or block diagram in the drawings is intended to illustrate the architecture, functionality, and/or operation of possible implementations of systems, methods, and computer program products according to aspects of the equine performance tracking and monitoring system. In this regard, each block may represent a module, segment, or portion of code, which comprises one or more executable instructions for implementing the specified logical function(s). In some implementations, the functions noted in the block may occur out of the order noted in the drawings. For example, two blocks shown in succession may, in fact, be executed substantially concurrently, or the blocks may sometimes be executed in the reverse order, depending upon the functionality involved. Each block and/or combination of blocks may be implemented by special purpose hardware-based systems (or combinations of special purpose hardware and computer instructions) that perform the specified functions or acts.

Examples, Components, and Alternatives

The following sections describe selected aspects of exemplary equine performance tracking and monitoring systems, as well as related systems and/or methods. The examples in these sections are intended for illustration and should not be interpreted as limiting the entire scope of the present disclosure. Each section may include one or more distinct embodiments or examples, and/or contextual or related information, function, and/or structure.

A. Illustrative HR Monitoring Strap

Figure 2:
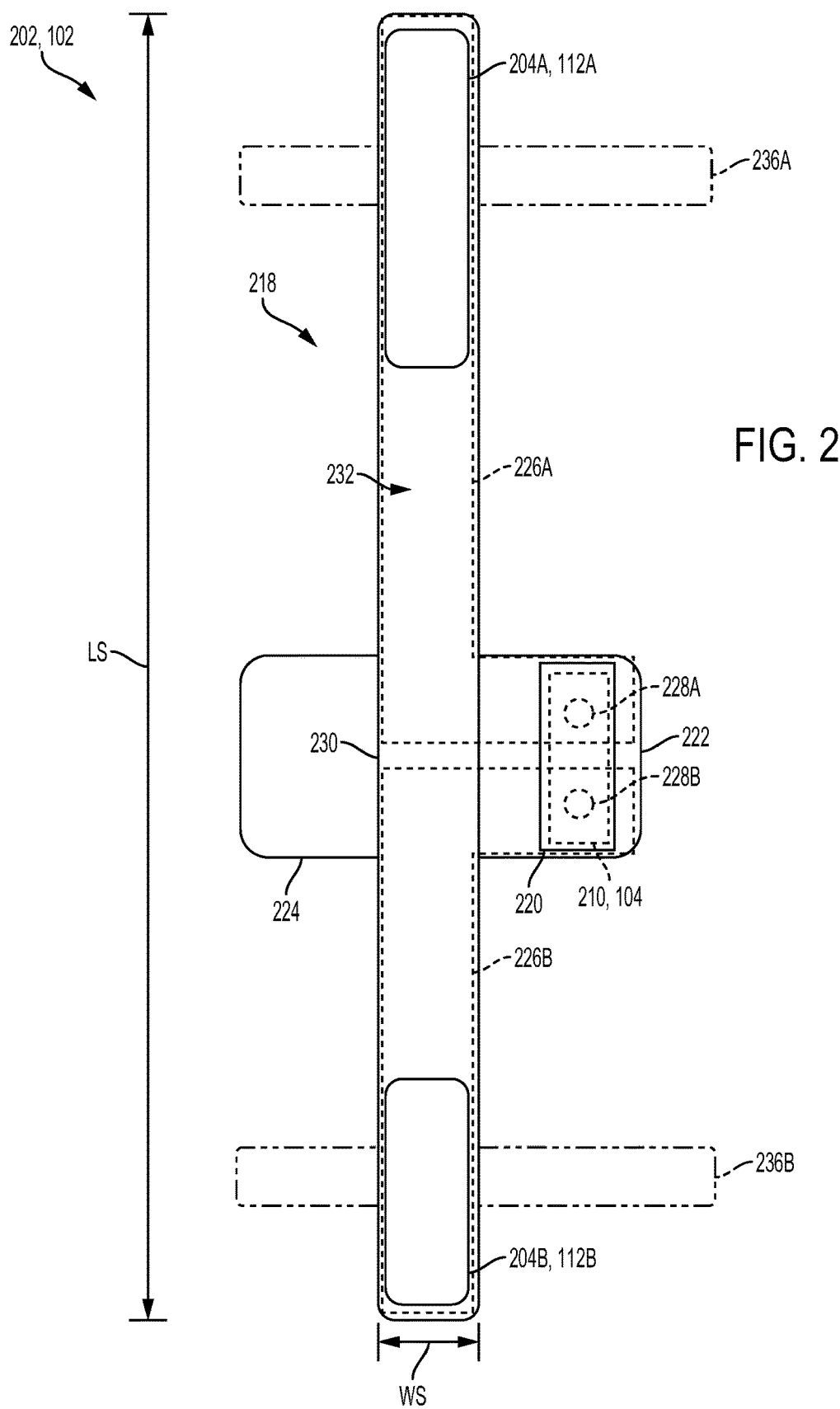
FIG. 2 is a side view of a heart rate monitoring strap for use with the present disclosure.

As shown in FIG. 2, this section describes an illustrative heart rate (HR) monitoring strap 202, which is an example of heart rate monitoring strap 102 suitable for use with an equine performance tracking and monitoring system such as system 100 described above. Accordingly, similar components may be labeled with similar reference numbers.

Heart rate monitoring strap 202 includes a central strap portion 218 having a length LS and a width WS. Heart rate monitoring strap 202 has a discrete length, and is configured to be attached between a horse and a girth portion of a saddle on the horse, on one side of the horse. As used herein, unless indicated otherwise, the term "girth portion" includes the girth itself and the attachment straps (e.g., billets) used to connect the girth to the saddle. In this example, heart rate monitoring strap 202 does not comprise a circumferential loop nor does it extend around the barrel of the horse. This ensures that heart rate monitoring strap 202 is as unobtrusive and as easy to use as possible. Because of its discrete length, heart rate monitoring strap 202 can be installed on the horse after the horse has been saddled or even once a rider has mounted. Furthermore, heart rate monitoring strap 202 avoids sensitive areas of the horse such as the withers. Length LS may be, for example, approximately 500 mm and width WS may be, for example, approximately 50 mm.

An upper electrode 204A and a lower electrode 204B are coupled to strap portion 218. The two electrodes have different sizes and/or shapes. In some embodiments, upper electrode 204A may be larger or longer than lower electrode 204B, e.g., to allow for variation in placement of the strap and/or for variation in the size and/or shape of the horse. In some examples, upper electrode 204A may span the full width WS of central strap portion 218 and also have a length of approximately 150 mm, while lower electrode 204B may span the full width WS of central strap portion 218 and also have a length of approximately 100 mm. In some embodiments electrodes 204A, 204B may be slightly narrower than central strap portion 218 and may have a width of approximately 48 mm. In some embodiments, a distance between a lower (i.e., inner) edge of electrode 204A and an upper (i.e., inner) edge of 204B may be approximately 250 mm.

Electrodes 204A, 204B may include any suitable sensors configured to detect signals (e.g., electrical signals) corresponding to the heart rate of animal 114. In some examples, electrodes 204A, 204B include conductive material, such as a conductive plastic or rubber. In some examples, electrodes 204A, 204B may include a conductive silver coating. Transmitter 210 may be protected by a transmitter cover 220. In this example transmitter 210 is located on a first flap 222 coupled to central strap portion 218. First flap 222 is configured to be removably attachable to a second flap 224 via any suitable fastening mechanism, for example, a hook-and-loop fastener (such as Velcro), buttons, snaps, magnets, high-friction materials, and/or the like, or any combination of these. Second flap 224 is coupled to central strap portion 218 and extends opposite first flap 222.

Electrodes 204A and 204B are electrically coupled to connectors 228A and 228B of transmitter 210 (see below) via respective, independent conductive layers of strap 202. In this example, the conductive layers are L-shaped pieces of conductive material, namely conductive members 226A and 226B. As depicted in FIG. 2, each of the conductive members extends along central strap portion 218 from its corresponding electrode toward the longitudinal center of central strap portion 218, then turns toward an outer edge of flap 222. At no point along either central strap portion 218 or flap 222 do conductive members 226A and 226B make contact with each other, thereby avoiding a direct electrical connection. Conductive members 226A and 226B may include any suitable material configured to carry an electrical signal while retaining a suitable level of flexibility, e.g., a wire or conductive foil. In this example, conductive members 226A and 226B comprise conductive rubber. Transmitter 210 couples to conductive members 226A and 226B via connectors (i.e., snaps) 228A and 228B, respectively. The conductive snaps provide both a physical attachment for transmitter 210 to flap 222 and an electrical connection between the transmitter and conductive members 226A and 226B. Snaps 228A and 228B may include any suitable structure or material configured to ensure both a physical and electrical connection between the transmitter and each of the conductive members. In some embodiments, snaps 228A and 228B may be approximately 100 mm apart. In some embodiments, snap 228A may be approximately 280 mm from an upper end of heart rate monitoring strap 202. In some embodiments, snap 228B may be approximately 183 mm from a lower end of heart rate monitoring strap 202.

Conductive members 226A and 226B are sandwiched between (e.g., encased within) a nonconductive base layer 230 and a nonconductive cover layer 232. Base layer 230 extends to the full length and width of central strap portion 218 (i.e. along length LS and across width WS) and along the full extent of flap 222. Cover layer 232 does not extend along the full length of central strap portion 218 and instead extends only along the portion of the central strap portion 218 that lies between electrodes 204A and 204B. Along this distance, cover layer 232 does extend across the full width of central strap portion 218 (i.e. width WS). Cover layer 232 also extends along the full extent of flap 222, though cover layer 232 may also have apertures through which snaps 228A and 228B may extend to couple transmitter 210 to conductive members 226A and 226B respectively. The two nonconductive layers (base layer 230 and cover layer 232) may include any suitable material configured to prevent the movement of an electrical signal and to provide some degree of environmental protection to the conductive members. For example, the two nonconductive layers may ensure that heart rate monitoring strap 202 is durable, weatherproof, and/or waterproof. Examples of suitable non-conductive material may include leather, or a fabric, e.g., a fabric including approximately 38% polyamide, 29% polyurethane, 20% elastane, and 13% polyester. The nonconductive layers may also be configured to provide the strap with a selected amount of stiffness. Each of the nonconductive layers may include the same or different materials.

Heart rate monitoring strap 202 is configured to fit underneath a girth portion on a horse when the horse is saddled (see FIGS. 8-13). Flaps 222 and 224 facilitate this placement by wrapping around the girth and/or billets to hold the heart rate monitoring strap in place on the horse. In some embodiments, nonconductive cover layer 232 may be further configured to provide the strap with a surface texture that will not cause excessive friction on the horse. In some embodiments, nonconductive base layer 230 may be further configured to provide the strap with a surface texture that will frictionally couple with the underside of the girth portion or saddle pad. In some examples, material on base layer 230 may couple with the material of the girth portion and/or the saddle pad or blanket to assist in holding heart rate monitoring strap 202 in place underneath the girth. For example, the base layer may include a hook-and-loop fastener material (for example, Velcro).

In some embodiments, heart rate monitoring strap 202 may include (optional) upper and lower connecting straps 236A and 236B. Upper and lower connecting straps 236A and 236B may be used to affix heart rate monitoring strap 202 more securely to the girth portion of the saddle. To facilitate this, connecting straps 236A and 236B may be configured to couple together, for example, using hook-and-loop fasteners or through use of a buckle and/or snap structure. In some embodiments, connecting straps 236A and 236B may be absent. In some embodiments, connecting straps 236A and 236B may be removably attachable to the main strap via any suitable fastening mechanism (e.g., a hook-and-loop fastener, buttons, snaps, magnets, etc.).

B. Method of Operation

Figure 3:
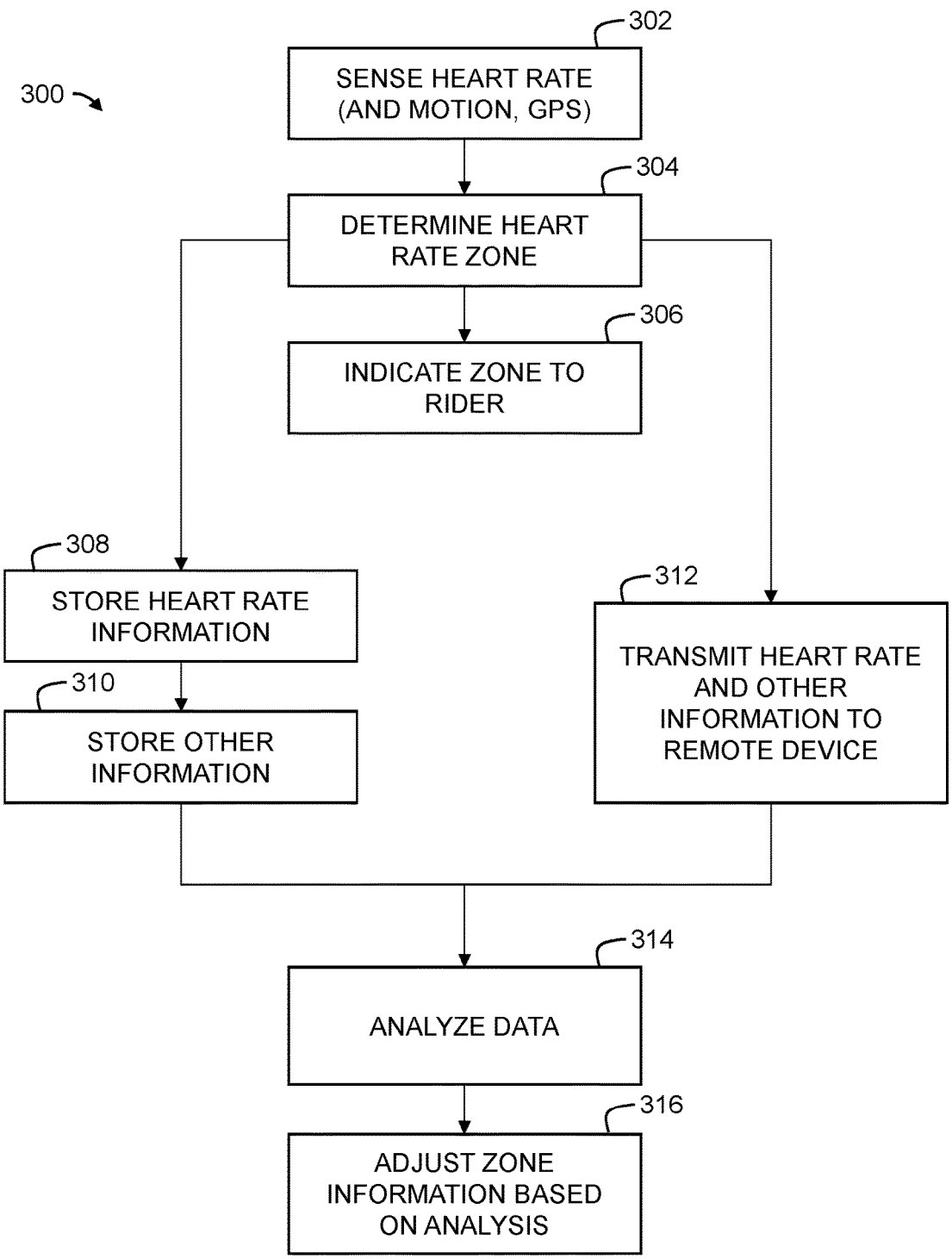
FIG. 3 is a flowchart depicting steps of an illustrative method for monitoring the heart rate of a horse.

As shown in FIG. 3, this section describes steps of an illustrative method or algorithm for monitoring and tracking the performance of an animal, such as a horse. Aspects of equine performance tracking and monitoring systems, such as system 100 depicted in FIG. 1, may be utilized in the method steps described below. Where appropriate, reference may be made to components and systems that may be used in carrying out each step. These references are for illustration, and are not intended to limit the possible ways of carrying out any particular step of the method.

FIG. 3 is a flowchart illustrating steps performed in an illustrative method, and may not recite the complete process or all steps of the method. FIG. 3 depicts multiple steps of a method, generally indicated at 300, which may be performed in conjunction with equine performance tracking and monitoring system 100, according to aspects of the present disclosure. Although various steps of method 300 are described below and depicted in FIG. 3, the steps need not necessarily all be performed, and in some cases may be performed in a different order than the order shown. In some examples, one or more steps of method 300 may be repeated.

At step 302 of method 300, the heart rate of a horse may be sensed, such as during a training session, using a monitoring device (e.g., heart rate monitoring strap 102 or heart rate monitoring strap 202). In some examples, step 302 includes the simultaneous sensing of motion (e.g., using accelerometers) and/or geolocation (e.g., using GPS). In some examples, step 302 includes sensing of a heart rate of a rider of the horse as well.

At step 304 of method 300, the horse's heart rate measured in step 302 is compared to a plurality of heart rate zones, and the corresponding zone is determined. For example, five zones may be established, each of which includes a range of heart rates (e.g., in beats per minute). The zones may be mutually exclusive, such that the zones do not overlap. Selected zones may be characterized by desirability during different activities or by their overall cardiovascular training effect on the animal, such as a "training for endurance" zone or a "resting" zone. Each zone may be assigned a color, for use in other steps.

Default heart rate zones may be established by one or more equine experts, such that the zones correspond to their intended use. This is in contrast to typical heart rate zone determinations, which are based on human cardiovascular performance. Horses have a much wider range of possible heart rates, and have a different physiology and biometric response as compared with humans. Accordingly, proper horse-specific heart rate zones are desirable. These default heart rate zones may be adjusted, based on inputs from a user (e.g., based on horse's age, training level, discipline, and empirical evidence), and/or by automatic means (as described below).

At step 306 of method 300, the current heart rate zone may be communicated to a rider of the horse, such as by visual and/or audible indication. For example, a watch or other portable device worn by the rider may include a display (in some embodiments, this may include wearable device 106 and/or portable electronic device 108). In some examples, a portion of the display may include a color corresponding to the present heart rate zone. In some examples, visual indication may include turning a portion of the display green whenever the horse is in a desired zone, turning a portion of the display red when the horse is in an undesired zone, and/or turning various portions of the display different colors for each zone to ensure the rider knows where the heart rate is relative to other zones (i.e., above or below). In some examples, a display screen may be used which includes information such as the actual numeric beats per minute, in addition to a predominant color indicating the zone. Preferably, the display or other indicator is located within the normal field of view of the rider, such that additional or out of the ordinary movements are not needed. Preferably, the indication is simple, such that the rider does not have to perform any additional mental steps to interpret the zone information (e.g., converting a beats per minute number to a zone range).

At step 308 of method 300, heart rate information may be stored. For example, heart rate data may be saved to an onboard nonvolatile storage device (e.g. on wearable device 106). At step 310, other information, such as GPS and accelerometer data, may be stored as well, and may be stored in a manner that correlates the heart rate, GPS, and accelerometer data (e.g., using time stamps).

At step 312 of method 300, the heart rate and other information may be transmitted to a remote device. For example, heart rate, GPS, and accelerometer data may be wirelessly transmitted from wearable device 106 to a portable electronic device 108, over a Bluetooth® and/or Bluetooth® LE wireless technology standard connection. This data may be transmitted in real time, and/or may be transmitted after the fact, such as by retrieving the data from wearable device 106.

At step 314 of method 300, the performance data may be analyzed. In some examples, analysis is done using machine learning algorithms trained to analyze equine performance information. In some examples, deep learning algorithms, such as artificial neural networks (e.g., supervised, unsupervised, and the like) are trained using a training set of human-verified data, combining accelerometer data, GPS positional and movement data, and horse heart rate over time and at high resolution. Each dataset is marked up to indicate known information such as type of exercise, external conditions, and expert insights based on the data. The learning models are thereby trained to recognize type and duration of exercise, as well as to generate various insights.

At step 316 of method 300, the heart rate zone definitions may be adjusted based on information determined from the analysis of step 314 and/or by a separate learning algorithm configured to analyze the empirical heart rate ranges for each animal. For example, a given horse may have a higher than normal maximum heart rate, as demonstrated by actual training information, which should cause the default heart rate zones to be adjusted upward.

C. Illustrative Graphical User Interface

As shown in FIG. 4, this section describes an illustrative graphical user interface (GUI) 500. GUI 500 is an example of GUI 130, described above. GUI 500 is an example of a GUI that is controlled by app 132 and appears on a portable electronic device such as device 108 to display information about one or more rides. GUIs having other configurations may be used to convey similar and/or related information.

Within GUI 500, a screen region 502 may display the date and/or time of the ride. A region 504 may display the duration of the ride, while a region 506 may display the total distance traveled during the ride. Region 504 may be configured to display the duration of the ride in any suitable format, for example, a 45-minute ride may show a duration of 00:45:00. Region 506 may configured to display the distance of the ride in any suitable format, for example, in kilometers or in miles. A region 508 may display the average and/or maximum speed traveled during the ride, for example, in kilometers per hour or in miles per hour.

A region 510 may display information about the horse, including, for example, the name of the horse, a picture of the horse, the average heart rate of the horse during the training session, and/or the maximum and/or minimum heart rate of the horse during the training session. Region 512 may display information about the rider, including, for example, the name of the rider, a picture of the rider, the average heart rate of the rider during the training session, and/or the maximum and/or minimum heart rate of the rider during the training session.

A screen region 514 may be configured to display a plurality of analyses of the ride. For example, region 514 may display a graph of the heart rate of both the horse and the rider over a period of time which may correspond to the duration of the ride, as shown in FIG. 4. Region 514 may be configured to be selectively transitioned between different screens (e.g., by a swiping gesture). Each screen may display a different kind of information, chart, and/or graph. Examples of information that may be displayed in region 514 include the heart rate of the horse and/or rider over time; the heart rate of the horse and the speed of the horse over time; a bar chart showing the amount of time spent in different heart rate zones; the heart rate of the horse over time overlaid onto which zone the heart rate is in; graphs of heart rate, speed, and/or gait vs. time; a map of the ride; a video of the ride; and/or the like, or any combination of these.

D. Data Processing System

Figure 5:
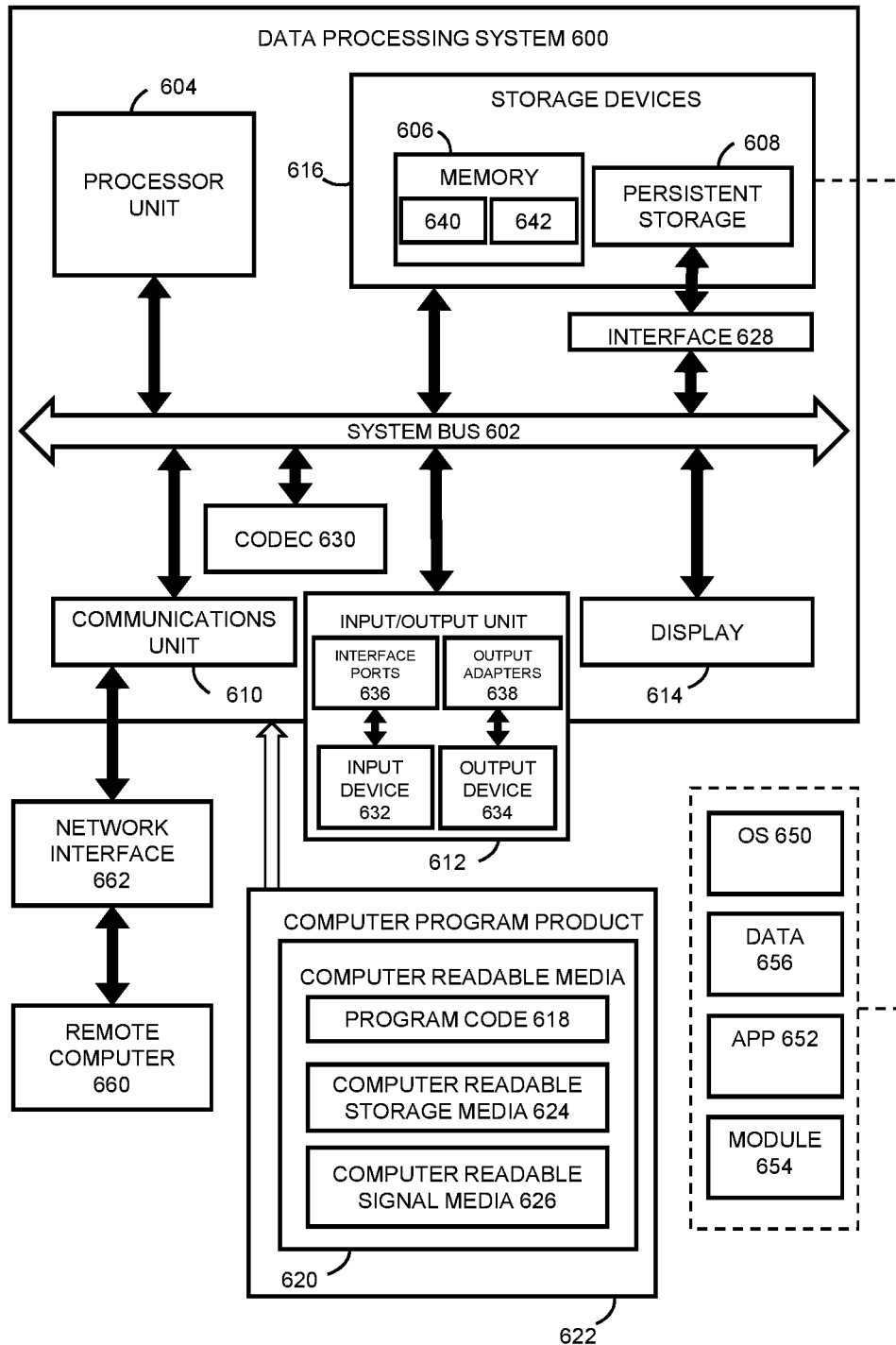
FIG. 5 is a schematic diagram of a data processing system suitable for use with the present disclosure.

As shown in FIG. 5, this example describes a data processing system 600 (also referred to as a computer) in accordance with aspects of the present disclosure. In this example, data processing system 600 is an illustrative data processing system suitable for implementing aspects of equine performance tracking and monitoring systems as described above. More specifically, in some examples, devices that are embodiments of data processing systems may comprise wearable device 106, transmitter 104, portable electronic devices 108, and/or data processing systems in network 110.

In this illustrative example, data processing system 600 includes a system bus 602 (also referred to as communications framework). System bus 602 may provide communications between a processor unit 604 (also referred to as a processor or processors), a memory 606, a persistent storage 608, a communications unit 610, an input/output (I/O) unit 612, a codec 630, and/or a display 614. Memory 606, persistent storage 608, communications unit 610, input/output (I/O) unit 612, display 614, and codec 630 are examples of resources that may be accessible by processor unit 604 via system bus 602.

Processor unit 604 serves to run instructions that may be loaded into memory 606. Processor unit 604 may comprise a number of processors, a multi-processor core, and/or a particular type of processor or processors (e.g., a central processing unit (CPU), graphics processing unit (GPU), etc.), depending on the particular implementation. Further, processor unit 604 may be implemented using a number of heterogeneous processor systems in which a main processor is present with secondary processors on a single chip. As another illustrative example, processor unit 604 may be a symmetric multi-processor system containing multiple processors of the same type.

Memory 606 and persistent storage 608 are examples of storage devices 616. A storage device may include any suitable hardware capable of storing information (e.g., digital information), such as data, program code in functional form, and/or other suitable information, either on a temporary basis or a permanent basis.

Storage devices 616 also may be referred to as computer-readable storage devices or computer-readable media. Memory 606 may include a volatile storage memory 640 and a non-volatile memory 642. In some examples, a basic input/output system (BIOS), containing the basic routines to transfer information between elements within the data processing system 600, such as during start-up, may be stored in non-volatile memory 642. Persistent storage 608 may take various forms, depending on the particular implementation.

Persistent storage 608 may contain one or more components or devices. For example, persistent storage 608 may include one or more devices such as a magnetic disk drive (also referred to as a hard disk drive or HDD), solid state disk (SSD), floppy disk drive, tape drive, Jaz drive, Zip drive, LS-60 drive, flash memory card, memory stick, and/or the like, or any combination of these. One or more of these devices may be removable and/or portable, e.g., a removable hard drive. Persistent storage 608 may include one or more storage media separately or in combination with other storage media, including an optical disk drive such as a compact disk ROM device (CD-ROM), CD recordable drive (CD-R Drive), CD rewritable drive (CD-RW Drive), and/or a digital versatile disk ROM drive (DVD-ROM). To facilitate connection of the persistent storage devices 608 to system bus 602, a removable or non-removable interface is typically used, such as interface 628.

Input/output (I/O) unit 612 allows for input and output of data with other devices that may be connected to data processing system 600 (i.e., input devices and output devices). For example, input device 632 may include one or more pointing and/or information-input devices such as a keyboard, a mouse, a trackball, stylus, touch pad or touch screen, microphone, joystick, game pad, satellite dish, scanner, TV tuner card, digital camera, digital video camera, web camera, and/or the like. These and other input devices may connect to processor unit 604 through system bus 602 via interface port(s) 636. Interface port(s) 636 may include, for example, a serial port, a parallel port, a game port, and/or a universal serial bus (USB).

Output devices 634 may use some of the same types of ports, and in some cases the same actual ports, as input device(s) 632. For example, a USB port may be used to provide input to data processing system 600 and to output information from data processing system 600 to an output device 634. Output adapter 638 is provided to illustrate that there are some output devices 634 (e.g., monitors, speakers, and printers, among others) which require special adapters. Output adapters 638 may include, e.g. video and sounds cards that provide a means of connection between the output device 634 and system bus 602. Other devices and/or systems of devices may provide both input and output capabilities, such as remote computer(s) 660. Display 614 may include any suitable human-machine interface or other mechanism configured to display information to a user, e.g., a CRT, LED, or LCD monitor or screen, etc.

Communications unit 610 refers to any suitable hardware and/or software employed to provide for communications with other data processing systems or devices. While communication unit 610 is shown inside data processing system 600, it may in some examples be at least partially external to data processing system 600. Communications unit 610 may include internal and external technologies, e.g., modems (including regular telephone grade modems, cable modems, and DSL modems), ISDN adapters, and/or wired and wireless Ethernet cards, hubs, routers, etc. Data processing system 600 may operate in a networked environment, using logical connections to one or more remote computers 660. A remote computer(s) 660 may include a personal computer (PC), a server, a router, a network PC, a workstation, a microprocessor-based appliance, a peer device, a smart phone, a tablet, another network note, and/or the like. Remote computer(s) 660 typically include many of the elements described relative to data processing system 600. Remote computer(s) 660 may be logically connected to data processing system 600 through a network interface 662 which is connected to data processing system 600 via communications unit 610. Network interface 662 encompasses wired and/or wireless communication networks, such as local-area networks (LAN), wide-area networks (WAN), and cellular networks. LAN technologies may include Fiber Distributed Data Interface (FDDI), Copper Distributed Data Interface (CDDI), Ethernet, Token Ring, and/or the like. WAN technologies include point-to-point links, circuit switching networks (e.g., Integrated Services Digital networks (ISDN) and variations thereon), packet switching networks, and Digital Subscriber Lines (DSL).

Codec 630 may include an encoder, a decoder, or both, comprising hardware, software, or a combination of hardware and software. Codec 630 may include any suitable device and/or software configured to encode, compress, and/or encrypt a data stream or signal for transmission and storage, and to decode the data stream or signal by decoding, decompressing, and/or decrypting the data stream or signal (e.g., for playback or editing of a video). Although codec 630 is depicted as a separate component, codec 630 may be contained or implemented in memory, e.g., non-volatile memory 642.

Non-volatile memory 642 may include read only memory (ROM), programmable ROM (PROM), electrically programmable ROM (EPROM), electrically erasable programmable ROM (EEPROM), flash memory, and/or the like, or any combination of these. Volatile memory 640 may include random access memory (RAM), which may act as external cache memory. RAM may comprise static RAM (SRAM), dynamic RAM (DRAM), synchronous DRAM (SDRAM), double data rate SDRAM (DDR SDRAM), enhanced SDRAM (ESDRAM), and/or the like, or any combination of these.

Instructions for the operating system, applications, and/or programs may be located in storage devices 616, which are in communication with processor unit 604 through system bus 602. In these illustrative examples, the instructions are in a functional form in persistent storage 608. These instructions may be loaded into memory 606 for execution by processor unit 604. Processes of one or more embodiments of the present disclosure may be performed by processor unit 604 using computer-implemented instructions, which may be located in a memory, such as memory 606.

These instructions are referred to as program instructions, program code, computer usable program code, or computer-readable program code executed by a processor in processor unit 604. The program code in the different embodiments may be embodied on different physical or computer-readable storage media, such as memory 606 or persistent storage 608. Program code 618 may be located in a functional form on computer-readable media 620 that is selectively removable and may be loaded onto or transferred to data processing system 600 for execution by processor unit 604. Program code 618 and computer-readable media 620 form computer program product 622 in these examples. In one example, computer-readable media 620 may comprise computer-readable storage media 624 or computer-readable signal media 626.

Computer-readable storage media 624 may include, for example, an optical or magnetic disk that is inserted or placed into a drive or other device that is part of persistent storage 608 for transfer onto a storage device, such as a hard drive, that is part of persistent storage 608. Computer-readable storage media 624 also may take the form of a persistent storage, such as a hard drive, a thumb drive, or a flash memory, that is connected to data processing system 600. In some instances, computer-readable storage media 624 may not be removable from data processing system 600.

In these examples, computer-readable storage media 624 is a physical or tangible storage device used to store program code 618 rather than a medium that propagates or transmits program code 618. Computer-readable storage media 624 is also referred to as a computer-readable tangible storage device or a computer-readable physical storage device. In other words, computer-readable storage media 624 is media that can be touched by a person.

Alternatively, program code 618 may be transferred to data processing system 600, e.g., remotely over a network, using computer-readable signal media 626. Computer-readable signal media 626 may be, for example, a propagated data signal containing program code 618. For example, computer-readable signal media 626 may be an electromagnetic signal, an optical signal, and/or any other suitable type of signal. These signals may be transmitted over communications links, such as wireless communications links, optical fiber cable, coaxial cable, a wire, and/or any other suitable type of communications link. In other words, the communications link and/or the connection may be physical or wireless in the illustrative examples.

In some illustrative embodiments, program code 618 may be downloaded over a network to persistent storage 608 from another device or data processing system through computer-readable signal media 626 for use within data processing system 600. For instance, program code stored in a computer-readable storage medium in a server data processing system may be downloaded over a network from the server to data processing system 600. The computer providing program code 618 may be a server computer, a client computer, or some other device capable of storing and transmitting program code 618.

In some examples, program code 618 may comprise be an operating system (OS) 650. Operating system 650, which may be stored on persistent storage 608, controls and allocates resources of data processing system 600. One or more applications 652 take advantage of the operating system's management of resources via program modules 654, and program data 656 stored on storage devices 616. OS 650 may include any suitable software system configured to manage and expose hardware resources of computer 600 for sharing and use by applications 652. In some examples, OS 650 provides application programming interfaces (APIs) that facilitate connection of different type of hardware and/or provide applications 652 access to hardware and OS services. In some examples, certain applications 652 may provide further services for use by other applications 652, e.g., as is the case with so-called "middleware." Aspects of present disclosure may be implemented with respect to various operating systems or combinations of operating systems.

The different components illustrated for data processing system 600 are not meant to provide architectural limitations to the manner in which different embodiments may be implemented. One or more embodiments of the present disclosure may be implemented in a data processing system that includes fewer components or includes components in addition to and/or in place of those illustrated for computer 600. Other components shown in FIG. 5 can be varied from the examples depicted. Different embodiments may be implemented using any hardware device or system capable of running program code. As one example, data processing system 600 may include organic components integrated with inorganic components and/or may be comprised entirely of organic components (excluding a human being). For example, a storage device may be comprised of an organic semiconductor.

In some examples, processor unit 604 may take the form of a hardware unit having hardware circuits that are specifically manufactured or configured for a particular use, or to produce a particular outcome or progress. This type of hardware may perform operations without needing program code 618 to be loaded into a memory from a storage device to be configured to perform the operations. For example, processor unit 604 may be a circuit system, an application specific integrated circuit (ASIC), a programmable logic device, or some other suitable type of hardware configured (e.g., preconfigured or reconfigured) to perform a number of operations. With a programmable logic device, for example, the device is configured to perform the number of operations and may be reconfigured at a later time. Examples of programmable logic devices include, a programmable logic array, a field programmable logic array, a field programmable gate array (FPGA), and other suitable hardware devices. With this type of implementation, executable instructions (e.g., program code 618) may be implemented as hardware, e.g., by specifying an FPGA configuration using a hardware description language (HDL) and then using a resulting binary file to (re)configure the FPGA.

In another example, data processing system 800 may be implemented as an FPGA-based (or in some cases ASIC-based), dedicated-purpose set of state machines (e.g., Finite State Machines (FSM)), which may allow critical tasks to be isolated and run on custom hardware. Whereas a processor such as a CPU can be described as a shared-use, general purpose state machine that executes instructions provided to it, FPGA-based state machine(s) are constructed for a special purpose, and may execute hardware-coded logic without sharing resources. Such systems are often utilized for safety-related and mission-critical tasks.

In still another illustrative example, processor unit 604 may be implemented using a combination of processors found in computers and hardware units. Processor unit 604 may have a number of hardware units and a number of processors that are configured to run program code 618. With this depicted example, some of the processes may be implemented in the number of hardware units, while other processes may be implemented in the number of processors.

In another example, system bus 602 may comprise one or more buses, such as a system bus or an input/output bus. Of course, the bus system may be implemented using any suitable type of architecture that provides for a transfer of data between different components or devices attached to the bus system. System bus 602 may include several types of bus structure(s) including memory bus or memory controller, a peripheral bus or external bus, and/or a local bus using any variety of available bus architectures (e.g., Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Personal Computer Memory Card International Association bus (PCMCIA), Firewire (IEEE 1394), and Small Computer Systems Interface (SCSI)).

Additionally, communications unit 610 may include a number of devices that transmit data, receive data, or both transmit and receive data. Communications unit 610 may be, for example, a modem or a network adapter, two network adapters, or some combination thereof. Further, a memory may be, for example, memory 606, or a cache, such as that found in an interface and memory controller hub that may be present in system bus 602.

The flowcharts and block diagrams described herein illustrate the architecture, functionality, and operation of possible implementations of systems, methods, and computer program products according to various illustrative embodiments. In this regard, each block in the flowcharts or block diagrams may represent a module, segment, or portion of code, which comprises one or more executable instructions for implementing the specified logical function or functions. It should also be noted that, in some alternative implementations, the functions noted in a block may occur out of the order noted in the drawings. For example, the functions of two blocks shown in succession may be executed substantially concurrently, or the functions of the blocks may sometimes be executed in the reverse order, depending upon the functionality involved.

E. Distributed Data Processing System

Figure 6:
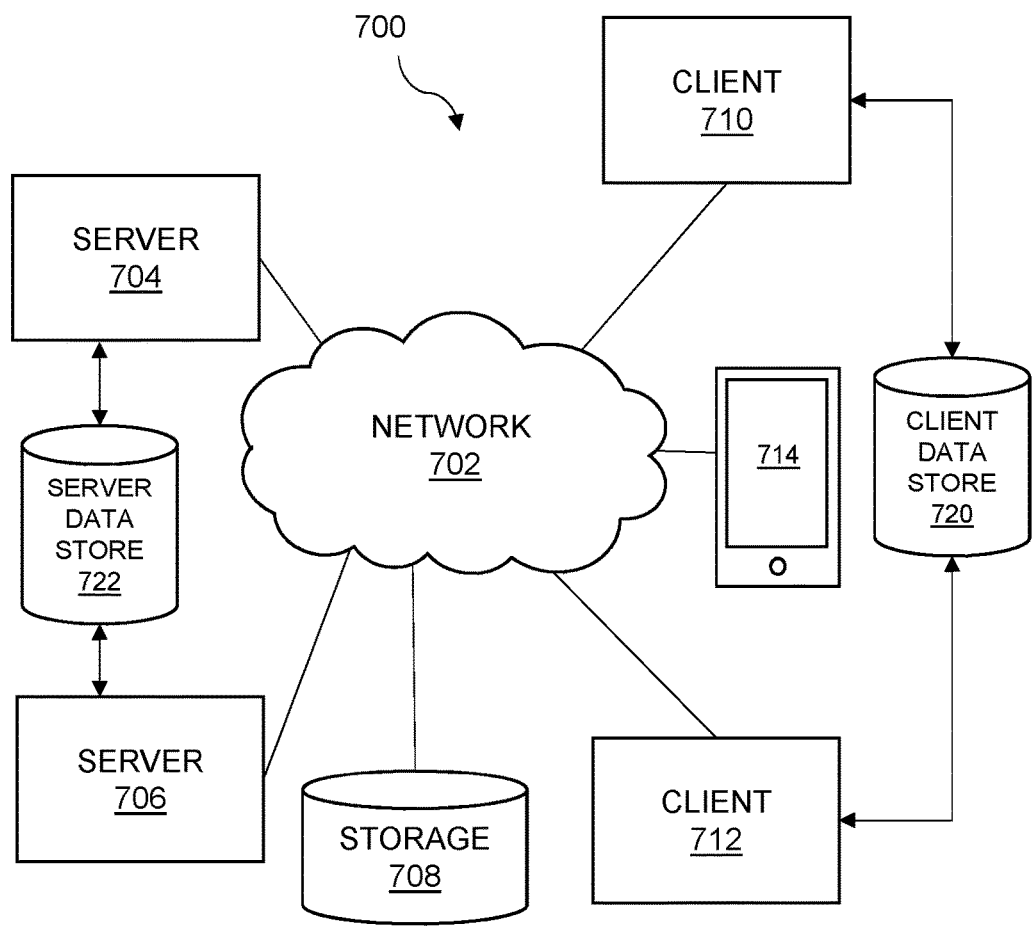
FIG. 6 is a schematic diagram of a distributed data processing system suitable for use with the present disclosure.

As shown in FIG. 6, this example describes a general network data processing system 700, interchangeably termed a network, a computer network, a network system, a distributed data processing system, or a distributed network, aspects of which may be included in one or more illustrative embodiments of the equine performance tracking and monitoring systems described above. For example, network 110 is a distributed data processing system, and various aspects of system 100 and method 300 may be carried out over the network. For example, selected analysis steps may be performed "in the cloud" and data may be communicated and stored over the network.

It should be appreciated that FIG. 6 is provided as an illustration of one implementation and is not intended to imply any limitation with regard to environments in which different embodiments may be implemented. Many modifications to the depicted environment may be made.

Network system 700 is a network of devices (e.g., computers), each of which may be an example of data processing system 600, and other components. Network data processing system 700 may include network 702, which is a medium configured to provide communications links between various devices and computers connected within network data processing system 700. Network 702 may include connections such as wired or wireless communication links, fiber optic cables, and/or any other suitable medium for transmitting and/or communicating data between network devices, or any combination thereof.

In the depicted example, a first network device 704 and a second network device 706 connect to network 702, as do one or more computer-readable memories or storage devices 708. Network devices 704 and 706 are each examples of data processing system 600, described above. In the depicted example, devices 704 and 706 are shown as server computers, which are in communication with one or more server data store(s) 722 that may be employed to store information local to server computers 704 and 706, among others. However, network devices may include, without limitation, one or more personal computers, mobile computing devices such as personal digital assistants (PDAs), tablets, and smartphones, handheld gaming devices, wearable devices, tablet computers, routers, switches, voice gates, servers, electronic storage devices, imaging devices, media players, and/or other networked-enabled tools that may perform a mechanical or other function. These network devices may be interconnected through wired, wireless, optical, and other appropriate communication links.

In addition, client electronic devices 710 and 712 and/or a client smart device 714, may connect to network 702. Each of these devices is an example of data processing system 600, described above regarding FIG. 5. Client electronic devices 710, 712, and 714 may include, for example, one or more personal computers, network computers, and/or mobile computing devices such as personal digital assistants (PDAs), smart phones, handheld gaming devices, wearable devices, and/or tablet computers, and the like. In the depicted example, server 704 provides information, such as boot files, operating system images, and applications to one or more of client electronic devices 710, 712, and 714. Client electronic devices 710, 712, and 714 may be referred to as "clients" in the context of their relationship to a server such as server computer 704. Client devices may be in communication with one or more client data store(s) 720, which may be employed to store information local to the clients (e.g., cookie(s) and/or associated contextual information). Network data processing system 700 may include more or fewer servers and/or clients (or no servers or clients), as well as other devices not shown.

In some examples, first client electric device 710 may transfer an encoded file to server 704. Server 704 can store the file, decode the file, and/or transmit the file to second client electric device 712. In some examples, first client electric device 710 may transfer an uncompressed file to server 704 and server 704 may compress the file. In some examples, server 704 may encode text, audio, and/or video information, and transmit the information via network 702 to one or more clients.

Client smart device 714 may include any suitable portable electronic device capable of wireless communications and execution of software, such as a smartphone or a tablet. Generally speaking, the term "smartphone" may describe any suitable portable electronic device configured to perform functions of a computer, typically having a touchscreen interface, Internet access, and an operating system capable of running downloaded applications. In addition to making phone calls (e.g., over a cellular network), smartphones may be capable of sending and receiving emails, texts, and multimedia messages, accessing the Internet, and/or functioning as a web browser. Smart devices (e.g., smartphones) may also include features of other known electronic devices, such as a media player, personal digital assistant, digital camera, video camera, and/or global positioning system. Smart devices (e.g., smartphones) may be capable of connecting with other smart devices, computers, or electronic devices wirelessly, such as through near field communications (NFC), the Bluetooth® and/or WiFi wireless technology standards, or mobile broadband networks. Wireless connectively may be established among smart devices, smartphones, computers, and/or other devices to form a mobile network where information can be exchanged.

Data and program code located in system 700 may be stored in or on a computer-readable storage medium, such as network-connected storage device 708 and/or a persistent storage 608 of one of the network computers, as described above, and may be downloaded to a data processing system or other device for use. For example, program code may be stored on a computer-readable storage medium on server computer 704 and downloaded to client 710 over network 702, for use on client 710. In some examples, client data store 720 and server data store 722 reside on one or more storage devices 708 and/or 608.

Network data processing system 700 may be implemented as one or more of different types of networks. For example, system 700 may include an intranet, a local area network (LAN), a wide area network (WAN), or a personal area network (PAN). In some examples, network data processing system 700 includes the Internet, with network 702 representing a worldwide collection of networks and gateways that use the transmission control protocol/Internet protocol (TCP/IP) suite of protocols to communicate with one another. At the heart of the Internet is a backbone of high-speed data communication lines between major nodes or host computers. Thousands of commercial, governmental, educational and other computer systems may be utilized to route data and messages. In some examples, network 702 may be referred to as a "cloud." In those examples, each server 704 may be referred to as a cloud computing node, and client electronic devices may be referred to as cloud consumers, or the like. FIG. 6 is intended as an example, and not as an architectural limitation for any illustrative embodiments.

F. Illustrative Method of Use

Figure 7:
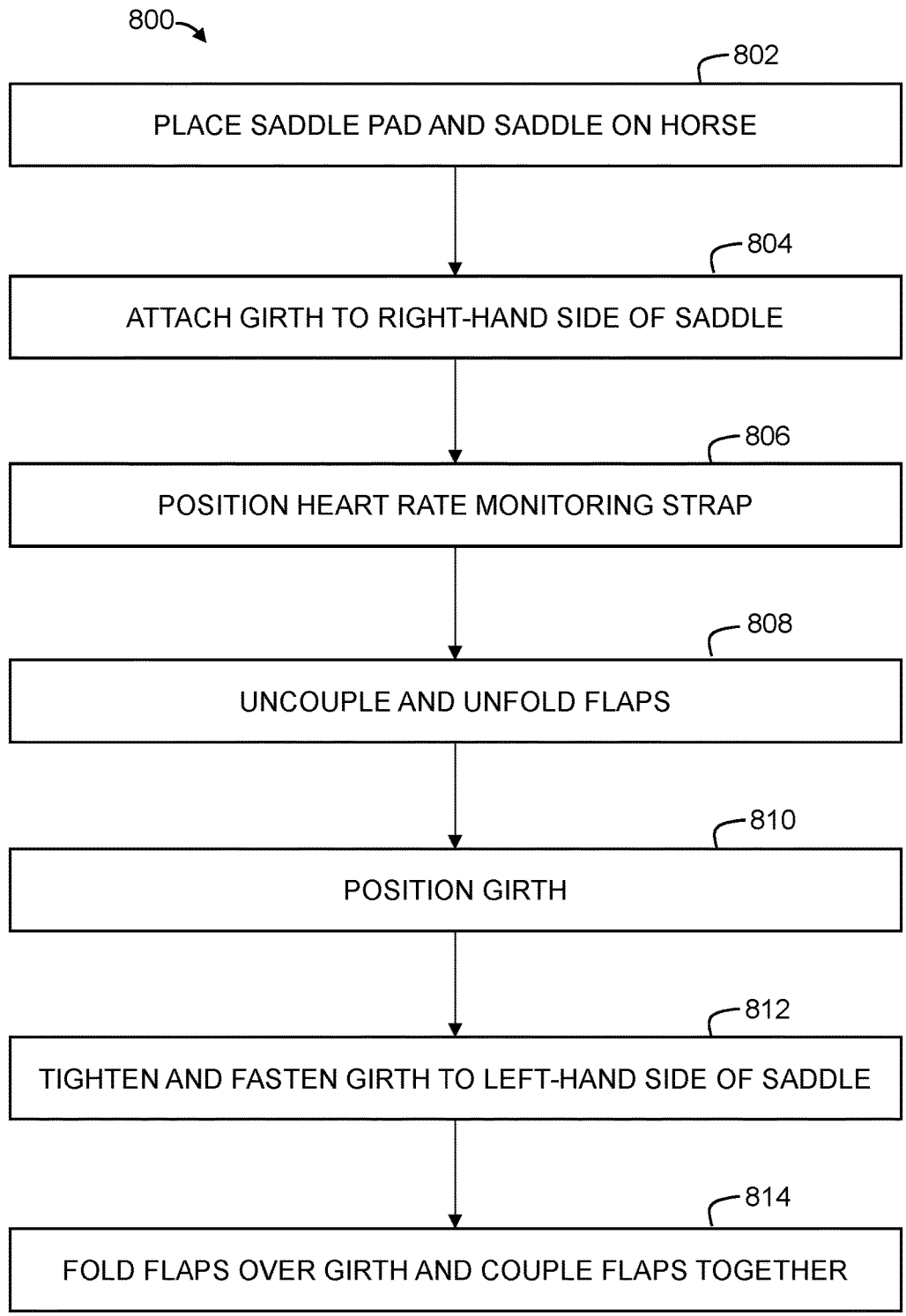
FIG. 7 is a flowchart depicting steps of an illustrative method of placement of a heart rate monitoring strap suitable for use with the present disclosure.

This section describes steps of an illustrative method 800 for installing a heart rate monitoring strap, such as heart rate monitoring strap 202 described above in relation to FIG. 2, on a horse 114; see FIG. 7. Aspects of an equine performance tracking and monitoring system such as system 100 may be utilized in the method steps described below. Where appropriate, reference may be made to components and systems that may be used in carrying out each step. These references are for illustration, and are not intended to limit the possible ways of carrying out any particular step of the method.

FIG. 7 is a flowchart illustrating steps performed in an illustrative method, and may not recite the complete process or all steps of the method. Although various steps of method 800 are described below and depicted in FIG. 7, the steps need not necessarily all be performed, and in some cases may be performed simultaneously or in a different order than the order shown.

Figure 8:
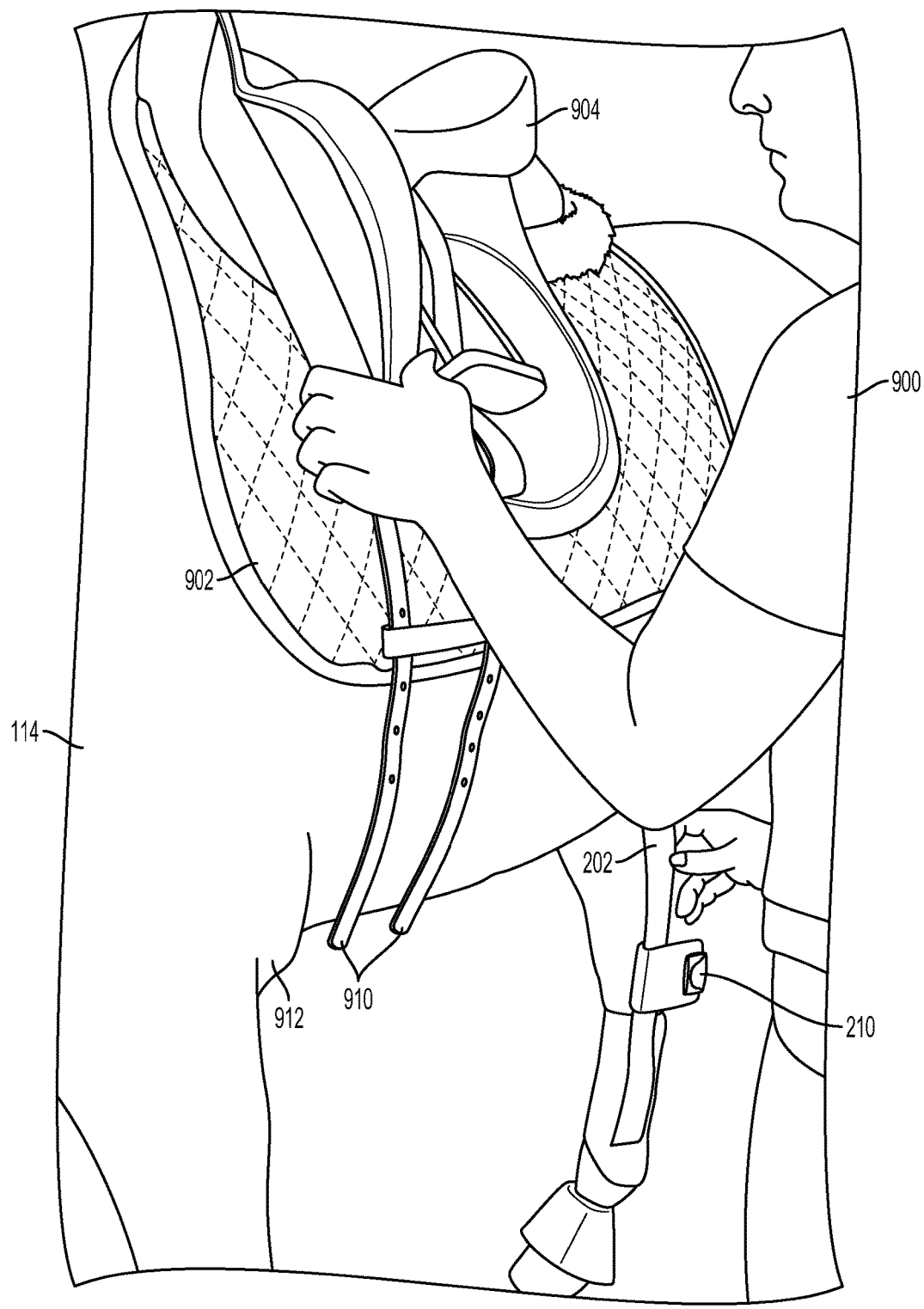
FIG. 8 shows a user and a horse demonstrating a first step in an illustrative method of use of a heart rate monitoring strap according to the present teachings.

At step 802, a user 900 of system 100 (e.g., a rider) places a saddle pad 902 and a saddle 904 onto horse 114. An embodiment of this step is depicted in FIG. 8. In some embodiments, system 100 may be used with an English saddle and, for ease of explanation, descriptions herein refer to the parts of an English saddle. In some embodiments, system 100 may be used with a western saddle and corresponding parts of the saddle may be referred to accordingly. For example, in some embodiments a saddle blanket may be used instead of saddle pad 902, a cinch, girth, or front cinch may be used instead of a girth 906, an off billet, off-side latigo, or a half-breed latigo may be used instead of a set of billets 908 on the right hand side of horse 114, and a latigo or cinch tie strap may be used instead of a set of billets 910 on the left hand side of horse 114.

At step 804, the user may attach girth 906 to billets 908 (not visible in FIGS. 8-13) on a right-hand side of saddle 904, if such a girth is not already attached or integrated with saddle 904.

Figure 9:
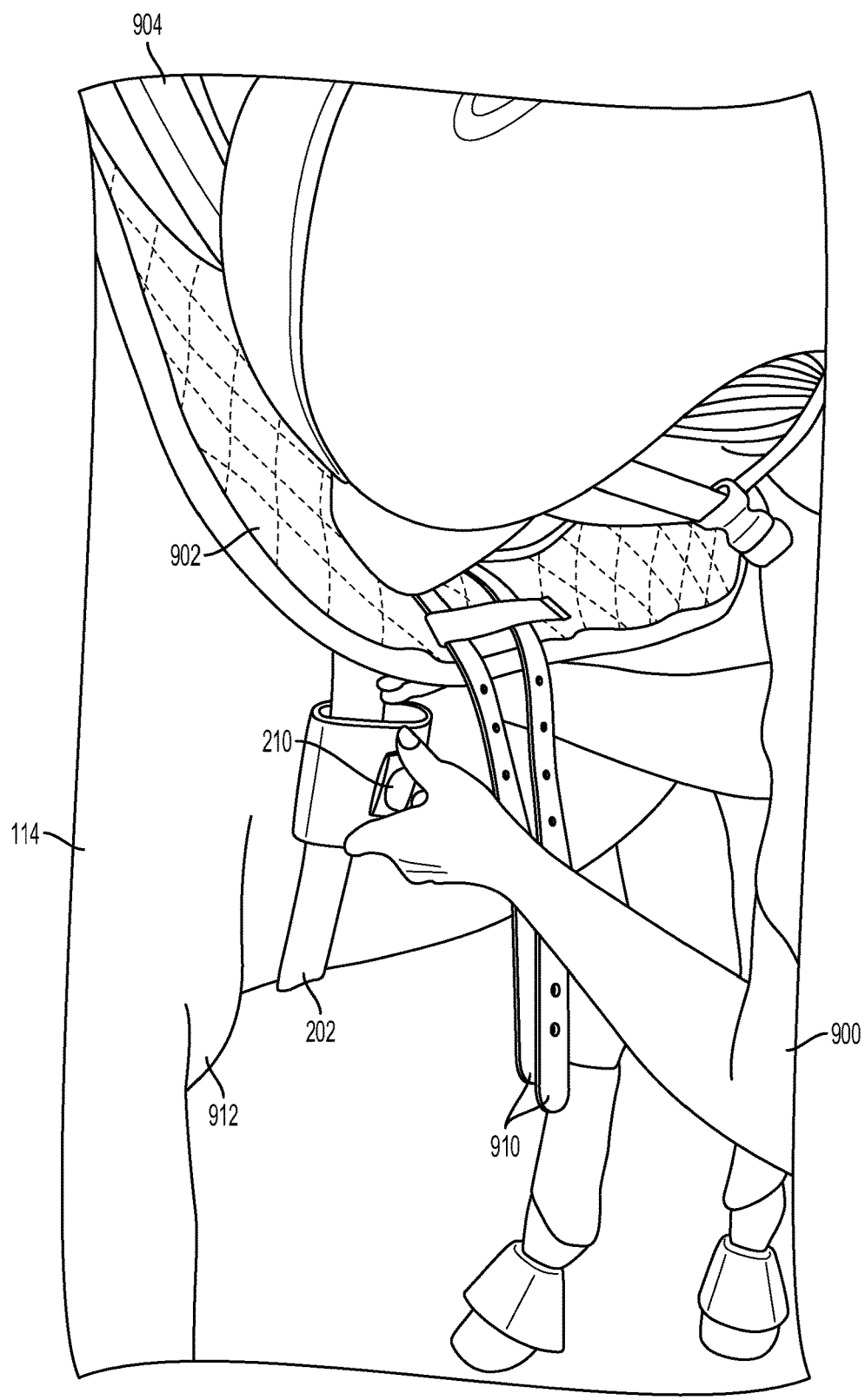
FIG. 9 shows the user and horse of FIG. 8 demonstrating a second step in the illustrative method of use of the heart rate monitoring strap.

At step 806, user 900 positions heart rate monitoring strap 202 against horse 114. This may include lifting an edge of saddle pad 902 and placing the upper part of the monitoring strap (including the portion of the strap where the upper electrode is located) underneath saddle pad 902. The lower end of the heart rate monitoring strap (including the portion of the strap where the lower electrode is located), is positioned behind a left elbow 912 of horse 114. An embodiment of this step is shown in FIG. 9.

Figure 10:
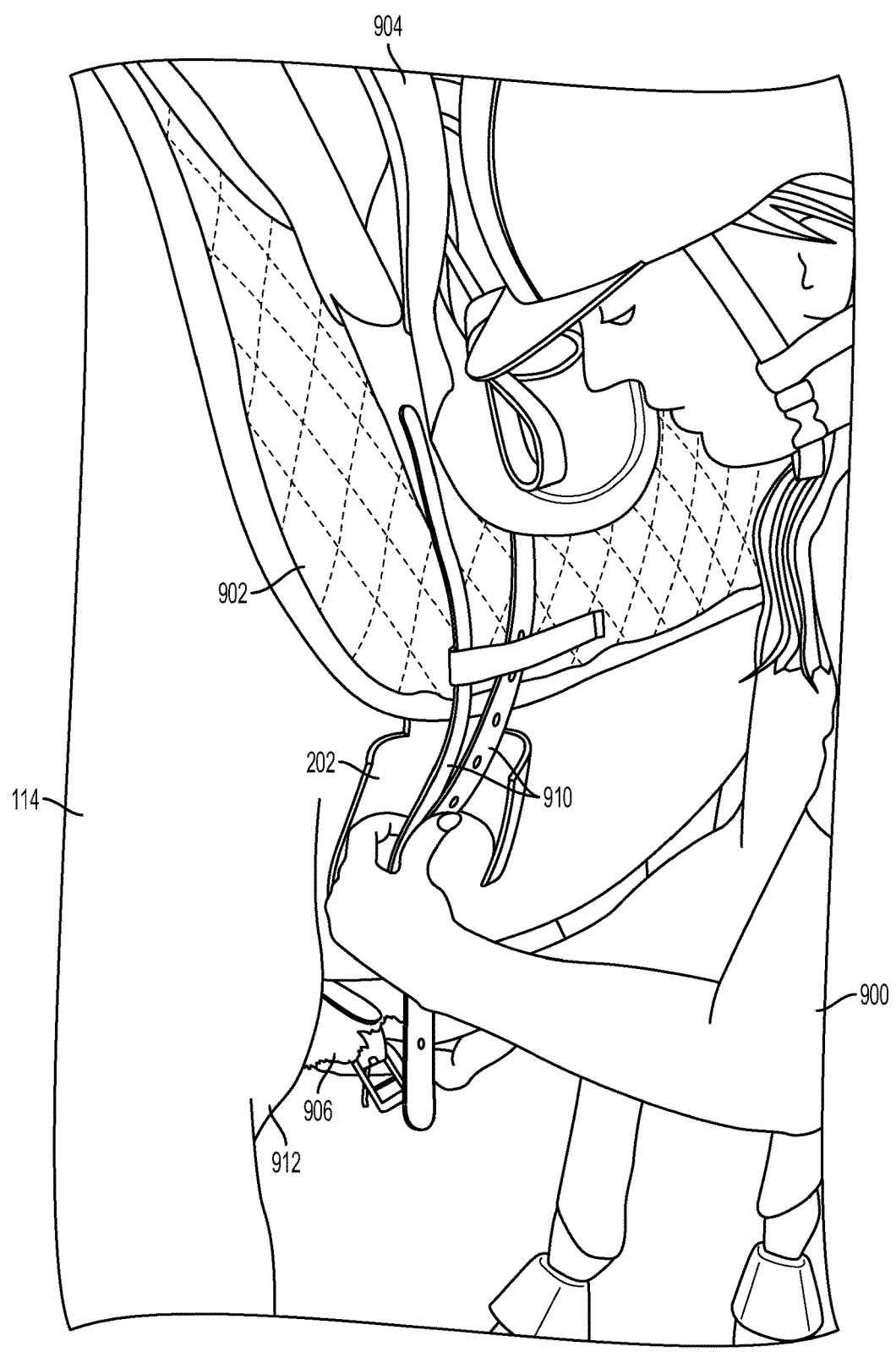
FIG. 10 shows the user and horse of FIG. 8 demonstrating a third step in the illustrative method of use of the heart rate monitoring strap.

At step 808, user 900 unfastens and unfolds flaps 222 and 224 of heart rate monitoring strap 202, if not already unfastened. At step 810, user 900 positions girth 906 and/or billets 910 over the top of heart rate monitoring strap 202. This may be done such that heart rate monitoring strap 202 is positioned underneath girth 906 and/or billets 910, and substantially aligned with a direction defined by girth 906 (i.e., transverse to the length of the horse). An embodiment of step 810 is shown in FIG. 10.

Figure 11:
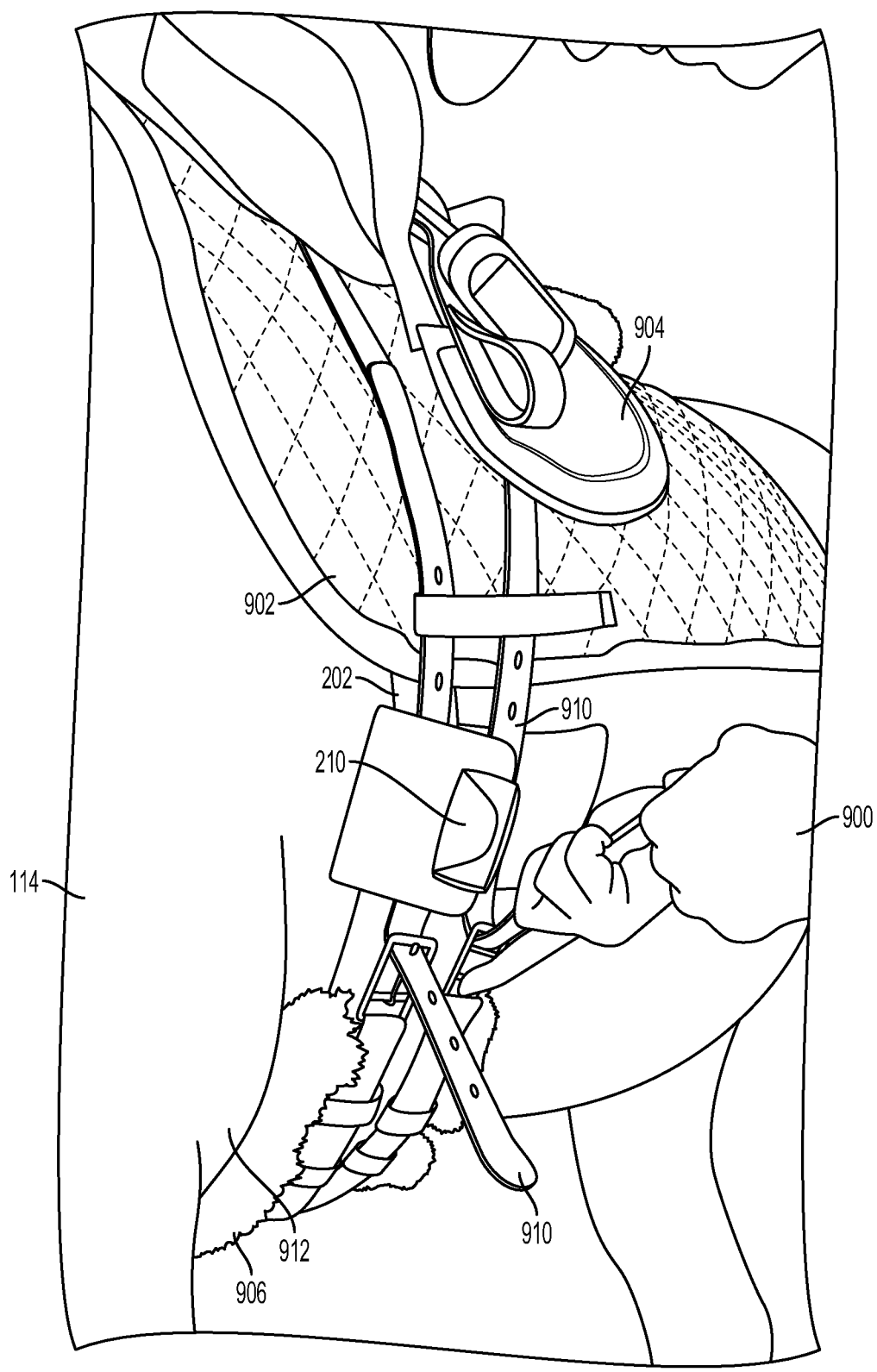
FIG. 11 shows the user and horse of FIG. 8 demonstrating a fourth step in the illustrative method of use of the heart rate monitoring strap.

At step 812, user 900 tightens and fastens girth 906 to billets 910 on the left-hand side of saddle 904. This may be done without substantially changing the position of the heart rate monitoring strap. An embodiment of step 812 is shown in FIG. 11.

Figure 12:
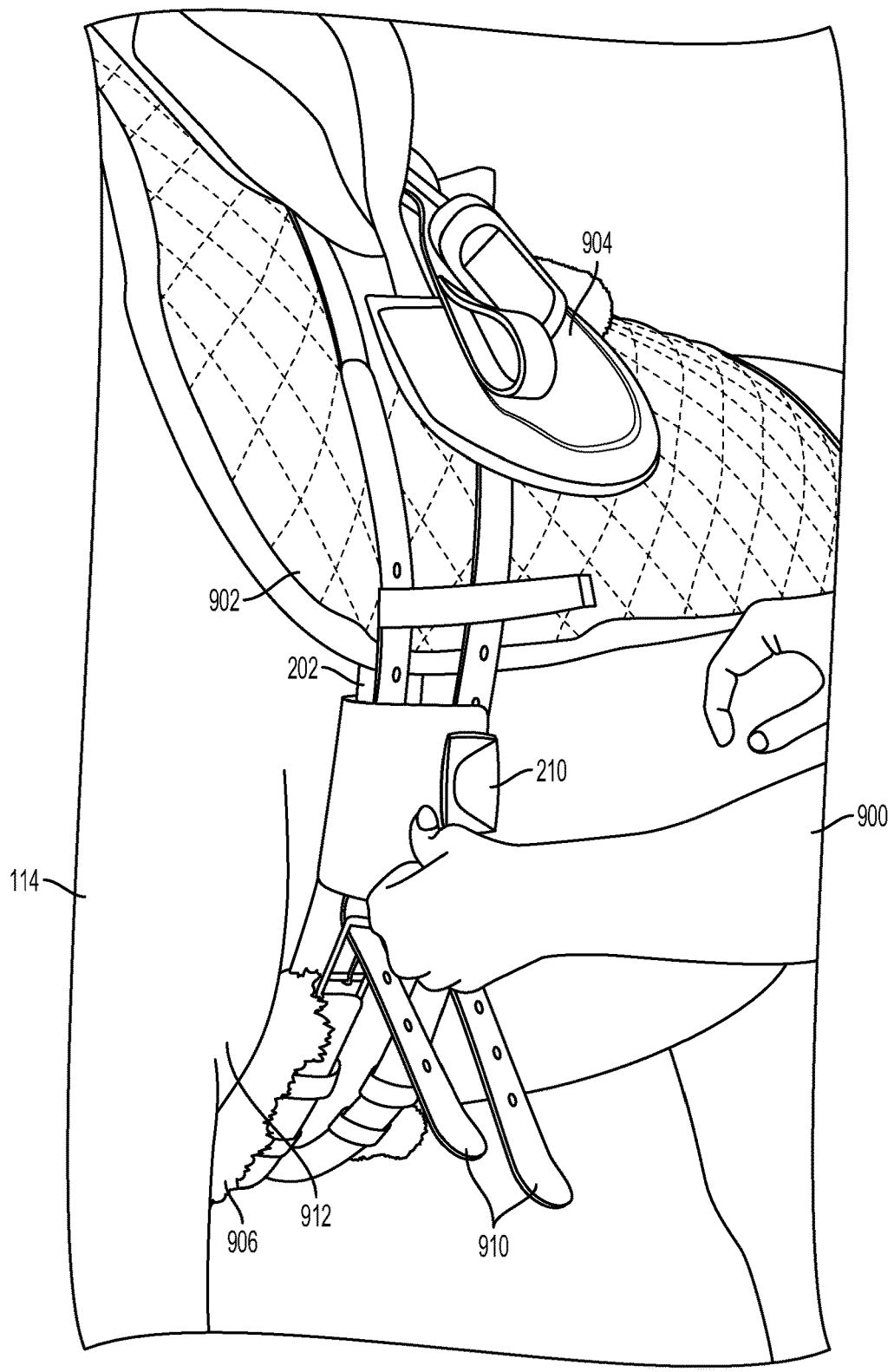
FIG. 12 shows the user and horse of FIG. 8 demonstrating a fifth step in the illustrative method of use of the heart rate monitoring strap.
Figure 13:
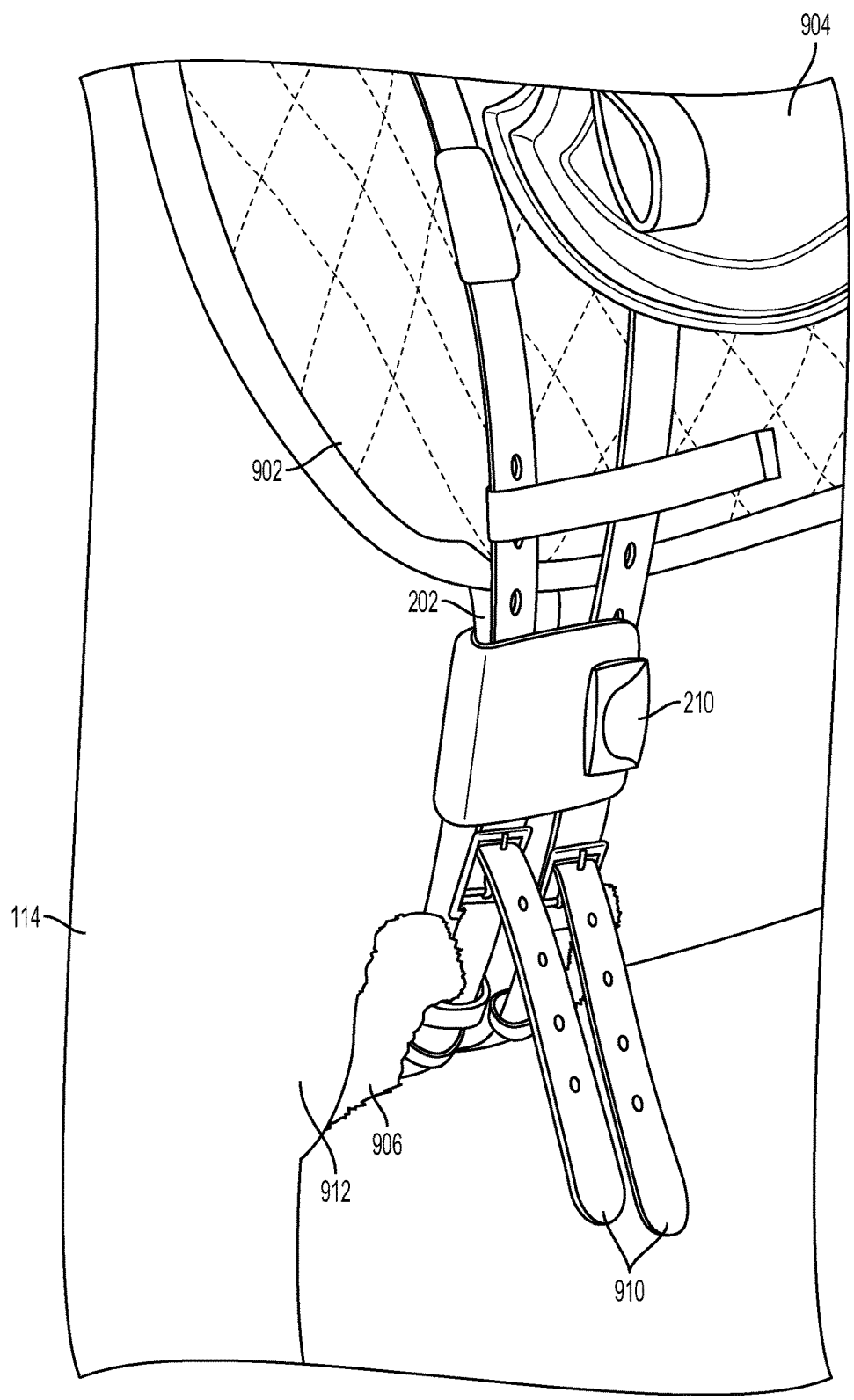
FIG. 13 shows the user and horse of FIG. 8 demonstrating a sixth step in the illustrative method of use of the heart rate monitoring strap.

At step 814, user 900 folds flaps 222 and 224 over girth 906 and/or billets 912. Flaps 222 and 224 fasten to each other to facilitate holding the heart rate monitoring strap in place against the horse and under the girth and/or billets. FIG. 12 shows an embodiment of step 814, and FIG. 13 shows heart rate monitoring strap 202 installed securely underneath the girth and saddle pad. In FIGS. 13 and 14, flaps 222 and 224 fasten around billets 912. In some embodiments, the flaps may fasten around the girth or another suitable portion of the horse's tack, or any combination thereof.

Method 800, as described above, is described in reference to the use of heart rate monitoring strap 202 in combination with a saddle. In some embodiments, heart rate monitoring strap 202 may be used in combination with a surcingle.

A method involving the use of a surcingle may include user 900 placing a surcingle on horse 114 and placing heart rate monitoring strap 202 on horse 114 under the surcingle, such that the lower end of the strap is behind left elbow 912 of horse 114. User 900 may then fasten the surcingle while heart rate monitoring strap 202 remains positioned between the surcingle and the horse, and substantially aligned with a direction defined by the surcingle (i.e., transverse to the length of the horse). Flaps 222 and 224 may be folded around and over the surcingle so that flaps 222 and 224 couple together. In some examples, user 900 may leave the heart rate monitoring strap in place for a significant period of time while the horse is not working in order to determine the resting heart rate of the horse. Knowing the horse's resting heart rate can be useful for understanding the horse's overall fitness. In some examples, using heart rate monitoring strap 202 with a surcingle may be useful for ground training (for example longing), in-hand training, training with a harness, or other forms of training for which a saddle is unnecessary or undesirable.

H. Additional Examples and Illustrative Combinations

This section describes additional aspects and features of an equine performance tracking and monitoring system, presented without limitation as a series of paragraphs, some or all of which may be alphanumerically designated for clarity and efficiency. Each of these paragraphs can be combined with one or more other paragraphs, and/or with disclosure from elsewhere in this application, including the materials incorporated by reference in the Cross-References, in any suitable manner. Some of the paragraphs below expressly refer to and further limit other paragraphs, providing without limitation examples of some of the suitable combinations.

A0. An equine performance tracking and monitoring system comprising:
an elongate heart rate (HR) monitoring strap having a first electrode at a first end portion and a second electrode at a second end portion, the first and second electrodes being electrically coupled to a transmitter disposed on the strap;
the HR monitoring strap being attachable to a horse by sandwiching the strap between a body of the horse and a girth portion of a saddle on the horse, such that the heart rate monitoring strap is against the body and the first and second electrodes monitor a heart rate of the horse; and
a wearable electronic device, wearable by a rider of the horse, having a display screen, and configured to receive heart rate signals from the transmitter of the HR monitoring strap;
wherein a processor of the wearable electronic device is configured to execute a set of stored instructions to determine a heart rate zone, selected from a plurality of defined heart rate zones, corresponding to a currently measured heart rate of the horse, and to cause the display screen to present, in real time, an indicator corresponding to the determined heart rate zone.

A1. The system of A0, the elongate HR monitoring strap further comprising a pair of flaps extending outward on opposing sides of the elongate strap, the pair of flaps being releasably securable to each other, such that the pair of flaps are configured to securely fasten around the girth portion when the HR monitoring strap is installed.

A2. The system of A1, wherein the pair of flaps comprise a hook-and-loop fastener.

A3. The system of A0, the wearable electronic device further comprising an accelerometer circuit including one or more accelerometers, the accelerometer circuit configured to provide sensed motion information of the horse.

A4. The system of A0, the wearable electronic device further comprising a heart rate sensor configured to detect a heart rate of the rider.

A5. The system of A4, wherein the wearable device further comprises a memory configured to store synchronized data corresponding to the heart rate of the rider and the heart rate of the horse.

A6. The system of A0, wherein the portable electronic device comprises a global positioning system (GPS) receiver.

A7. The system of A0, wherein the indicator comprises a screen display element of a graphical user interface (GUI).

A8. The system of A0, wherein each zone in the plurality of defined heart rate zones is adjustable.

A9. The system of A8, wherein the plurality of defined heart rate zones are automatically adjusted by the system based on actual heart rate data for a given horse.

B0. A heart rate monitoring system configured to measure the heart rate and other physical characteristics of a horse, the system comprising:
a discrete heart rate (HR) monitoring strap configured to fit between a horse and a girth portion of a saddle on the horse, the strap including at least two spaced-apart electrodes;
a pair of flaps extending from opposite sides of the strap, the pair of flaps being configured to wrap around the girth portion and fasten to each other, thereby holding the strap relative to the girth portion;
a wearable electronic device, wearable by a rider of the horse and configured to receive wireless communications;
a transmitter attached to one flap of the pair of flaps and in electrical communication with the at least two electrodes, the transmitter configured to transmit horse heart rate information wirelessly to the wearable electronic device; and
a computer application of the wearable electronic device configured to process the horse heart rate information from the transmitter and display the processed horse heart rate information on a screen of the wearable electronic device.

B1. The system of B0 wherein the strap includes material configured to hold the strap in place by engaging with the material of the girth portion.

B2. The system of B0 wherein the at least two electrodes include two electrodes having significantly different sizes.

B3. The system of B2, wherein a larger of the two electrodes is positioned higher than a smaller of the two electrodes.

B4. The system of B3 wherein the larger of the two electrodes is positioned under a saddle pad and the smaller of the two electrodes is positioned under the girth portion and behind a left elbow of the horse.

B5. The system of B0 wherein the transmitter is electrically connected to each of the electrodes by a respective conductive member.

B6. The system of B5, wherein the conductive members comprise conductive rubber.

B7. The system of B0, the wearable electronic device further comprising a heart rate monitoring sensor configured to detect rider heart rate information.

B8. The system of B7, wherein the computer application of the wearable electronic device is further configured to process the rider heart rate information and display the processed rider heart rate information on the screen of the wearable electronic device with the processed horse heart rate information.

B9. The system of B7, wherein the horse heart rate information and the rider heart rate information are stored in a memory of the wearable electronic device for later analysis.

C0. A method of monitoring a heart rate of a horse using a heart rate monitoring system, the method comprising:
sensing a heart rate of a horse, using electrodes coupled to a strap to sense the heart rate, wherein the strap has a discrete length and is positioned between the horse and a girth portion of a saddle on one side of the horse;
determining a heart rate zone based on a comparison of horse heart rate information from the electrodes with stored horse heart rate zone information;
indicating, in real time, the horse heart rate zone on a screen display of a local electronic device visible to a rider of the horse;

communicating the horse heart rate information to a remote electronic device; and adjusting the stored horse heart rate zone information based on an analysis of the communicated horse heart rate information.

C1. The method of C0, wherein the local electronic device comprises a global positioning system (GPS) receiver.

C2. The method of C0, wherein the local electronic device is wearable by the rider.

C3. The method of C0, wherein the remote electronic device is part of a distributed data processing system.

C4. The method of C0, wherein the horse heart rate information is stored in a memory of the local electronic device.

C4. The method of C0, further comprising measuring a heart rate of the rider using a sensor of the local electronic device.

C5. The method of C4, further comprising indicating, in real time, information relating to the rider heart rate on the screen display of the local electronic device.

D0. A method for installing a heart rate monitoring strap on a horse, the method comprising:
placing a saddle pad and a saddle on a horse;
attaching a girth to a right side of the saddle using first billets;
placing a heart rate monitoring strap on an exterior surface of the horse such that an upper end of the strap is under the saddle pad and a lower end of the strap is behind a left elbow of the horse;
positioning the girth around the horse and over the lower end of the strap;
attaching the girth to a left side of the saddle using second billets, the girth and first and second billets collectively defining a girth portion of the saddle, while the strap remains positioned between the girth portion and the horse, the strap being substantially aligned with a direction defined by the girth; and
folding two flaps attached to opposing edges of the strap around the girth portion and fastening distal ends of the flaps together.

E0. A method for monitoring a heart rate of a horse over the course of a plurality of rides comprising:
using a heart rate monitoring system to measure a heart rate of a horse during each ride of a plurality of rides; and
using information provided by the heart rate monitoring system to determine and display characteristics of each of the plurality of rides on a screen display of a portable electronic device;
wherein using the heart rate monitoring system includes installing a first heart rate monitoring strap on a horse by:
placing a saddle pad and a saddle on a horse;
attaching a girth to a right side of the saddle using first billets;
placing the first heart rate monitoring (HRM) strap on an exterior surface of the horse such that an upper end of the first HRM strap is under the saddle pad and a lower end of the first HRM strap is behind a left elbow of the horse;
positioning the girth around the horse and over the lower end of the first HRM strap;
attaching the girth to a left side of the saddle using second billets, the girth and first and second billets collectively defining a girth portion of the saddle, while the HRM strap remains positioned between the girth portion and the horse, the HRM strap being substantially aligned with a direction defined by the girth; and
folding two flaps attached to opposing edges of the HRM strap around the girth portion and fastening distal ends of the flaps together.

E1. The method of E0, further including using a second heart rate monitoring (HRM) strap of the heart rate monitoring system to measure a heart rate of a rider during each ride of the plurality of rides.

E2. The method of E0 further comprising establishing a resting heart rate of the horse by:
placing a surcingle on the horse;
placing the first HRM strap on the horse under the surcingle such that the lower end of the first HRM strap is behind the left elbow of the horse;
fastening the surcingle while the first HRM strap remains positioned between the surcingle and the horse, with the first HRM strap generally oriented in a direction defined by the surcingle; and
monitoring the heart rate of the horse while the horse is resting.

E3. The method of E0 wherein the characteristics of each ride include one or more characteristics chosen from a list consisting of a duration, an intensity, a style, and a location.

Advantages, Features, Benefits

The different embodiments and examples of the equine performance tracking and monitoring systems described herein provide several advantages over known solutions for monitoring the performance of a horse. For example, illustrative embodiments and examples described herein allow a trainer to monitor key aspects of a horse's fitness over the course of a training session or over the course of several training sessions.

Additionally, and among other benefits, illustrative embodiments and examples described herein allow a rider to view both the heart rate of the horse and the heart rate of the rider during the training session and/or after the training session.

Additionally, and among other benefits, illustrative embodiments and examples described herein allow a rider to view both the heart rate of the horse and the heart rate of the rider at the same time and/or on the same graphical display.

Additionally, and among other benefits, illustrative embodiments and examples described herein allow a rider to update how they ride or train their horse mid-ride in response to highly accurate heart rate information. In doing so, a rider can promote the overall health and wellbeing of their horses.

Additionally, and among other benefits, illustrative embodiments and examples described herein allow a rider to know, in the moment, the appropriate level of training for each of their horses, instead of being left to guess.

Additionally, and among other benefits, illustrative embodiments and examples described herein allow a rider to monitor the heart rate of a horse both during training and when a horse is at rest to gain an indicator of the wellness and overall wellbeing of the horse.

Additionally, and among other benefits, illustrative embodiments and examples described herein facilitate tracking of fitness variability, adjustment of training rigor, and early detection of injury/illness.

Additionally, and among other benefits, illustrative embodiments and examples described herein combine heart rate during training with movement data to allow improved insights by riders and trainers.

Additionally, and among other benefits, illustrative embodiments and examples described herein allow trainers and owners to improve the overall health and fitness of their horses through measurable data.

Additionally, and among other benefits, illustrative embodiments and examples described herein allow information about a particular ride or horse to be stored on a network for further analysis or comparison with other horses or other rides.

Additionally, and among other benefits, illustrative embodiments and examples described herein allow the application of machine learning to the recorded movement and heart rate data, thereby determining the type of movement and exercises performed, duration of those exercises, and the horse's exertion level and recovery patterns during the ride.

Additionally, and among other benefits, illustrative embodiments and examples described herein allow the analysis of ride information by machine learning to be used to generate written and/or visual advice and analysis.

Additionally, and among other benefits, illustrative embodiments and examples described herein allow a rider to view previous sessions and/or share information about training sessions with anyone they choose, both in real time (as they ride) and for previous sessions.

Additionally, and among other benefits, illustrative embodiments and examples described herein allow a rider and/or owner to view all the data about a particular horse and may also allow a rider and/or owner to view a dataset of expert-collected horse training data for comparison with their own horses.

Additionally, and among other benefits, illustrative embodiments and examples described herein allow reliable measurement of a horse's heart rate regardless of small variations in placement of the heart rate monitoring strap due to variations in placement method and/or variations in the size and/or shape of the horse. In particular, the placement and size of the electrodes on the heart rate monitoring strap provide accurate and clean readings, based on testing conducted using ECG technology.

Additionally, and among other benefits, illustrative embodiments and examples described herein allow dependable measurement of a horse's heart rate regardless of the movement of the horse by ensuring that the heart rate monitoring strap remains in place despite movement of the horse.

Additionally, and among other benefits, illustrative embodiments and examples described herein facilitate dependable measurement of a horse's heart rate using an unobtrusive and easy to use heart rate monitoring strap. The heart rate monitoring strap is easy to put on the horse and easy to take off of the horse, because it is only on the left side of the horse. In addition, the heart rate monitoring strap can be put on after saddling the horse and/or can even be put on the horse by another person after the rider has mounted the horse. This is in contrast, for example, with a piece that goes all the way around the barrel of the horse, which could only be put on before saddling the horse.

Additionally, and among other benefits, illustrative embodiments and examples described herein allow dependable measurement of a horse's heart rate without rubbing or irritating the horse. For example, the heart rate monitoring strap does not contact the withers, spine, and/or top of the horse, which are sensitive areas of the horse. The discrete length of the heart rate monitoring strap also minimizes the amount of equipment on the horse which decreases the likelihood of "hot spots" developing, equipment rubbing the horse, and/or other aspects of the equipment irritating the horse.

Additionally, and among other benefits, illustrative embodiments and examples described herein allow a rider to reliably and accurately measure the heart rate of the horse without concern that the equipment may negatively impact the horse.

Additionally, and among other benefits, illustrative embodiments and examples described herein allow a rider to view the heart rate of the horse or other in-ride analysis without large or unusual movements of the rider.

Additionally, and among other benefits, illustrative embodiments and examples described herein allow a rider to easily interpret the in-ride analysis and/or heart rate information through use of simple and/or easily understood visual and/or audial information.

No known system or device can perform these functions, particularly in the moment, during the ride. Thus, the illustrative embodiments and examples described herein are particularly useful for in-ride performance tracking and monitoring. However, not all embodiments and examples described herein provide the same advantages or the same degree of advantage.

CONCLUSION

The disclosure set forth above may encompass multiple distinct examples with independent utility. Although each of these has been disclosed in its preferred form(s), the specific embodiments thereof as disclosed and illustrated herein are not to be considered in a limiting sense, because numerous variations are possible. To the extent that section headings are used within this disclosure, such headings are for organizational purposes only. The subject matter of the disclosure includes all novel and nonobvious combinations and subcombinations of the various elements, features, functions, and/or properties disclosed herein. The following claims particularly point out certain combinations and subcombinations regarded as novel and nonobvious. Other combinations and subcombinations of features, functions, elements, and/or properties may be claimed in applications claiming priority from this or a related application. Such claims, whether broader, narrower, equal, or different in scope to the original claims, also are regarded as included within the subject matter of the present disclosure.

What is claimed is:

1. An equine performance tracking and monitoring system comprising:
    an elongate heart rate (HR) monitoring strap having a first electrode at a first end portion and a second electrode at a second end portion, the first and second electrodes being electrically coupled to a transmitter;
    one or more flaps, each extending outward from a long edge of the elongate HR monitoring strap, wherein the HR monitoring strap is configured to attach to a horse by sandwiching the strap between a body of the horse and a girth portion of a saddle on the horse with the one or more flaps releasably fastened around the girth portion of the saddle, such that the heart rate monitoring strap is against the body of the horse and extends only partially along one outboard side of the body of the horse, and wherein the first and second electrodes monitor a heart rate of the horse; and
    a wearable electronic device, wearable by a rider of the horse, having a display screen and configured to receive heart rate signals from the transmitter of the HR monitoring strap;
    wherein a processor of the wearable electronic device is configured to execute a set of stored instructions to determine a heart rate zone, selected from a plurality of defined heart rate zones, corresponding to a currently measured heart rate of the horse, and to cause the display screen to present, in real time, an indicator corresponding to the determined heart rate zone.

2. The system of claim 1, wherein the transmitter is disposed on one of the one or more flaps.

3. The system of claim 1, the wearable electronic device further comprising a heart rate sensor configured to detect a heart rate of the rider and a memory configured to store synchronized data corresponding to the heart rate of the rider and the heart rate of the horse.

4. The system of claim 1, the wearable electronic device further comprising an accelerometer circuit including one or more accelerometers, the accelerometer circuit configured to provide sensed motion information of the horse.

5. The system of claim 1, wherein the indicator comprises a screen display element of a graphical user interface (GUI).

6. The system of claim 1, wherein each zone in the plurality of defined heart rate zones is adjustable.

7. The system of claim 6, wherein the plurality of defined heart rate zones are automatically adjusted by the system based on actual heart rate data for a given horse.

8. A system for measuring physical characteristics of a horse, the system comprising:
a heart rate (HR) monitoring strap configured to fit between a horse and a girth portion of a saddle on the horse, wherein the strap includes at least two spaced-apart electrodes and has a length configured to be shorter than a circumference of a body of the horse, such that the strap extends only partially along one outboard side of the body of the horse when installed;
one or more flaps, each extending laterally from a long edge of the strap, the one or more flaps being configured to fasten around the girth portion of the saddle, thereby securing the strap relative to the girth portion of the saddle;
a wearable electronic device, wearable by a rider of the horse and configured to receive wireless communications;
a transmitter coupled to the HR monitoring strap and in electrical communication with the at least two electrodes, the transmitter configured to transmit horse heart rate information wirelessly to the wearable electronic device; and
a computer application of the wearable electronic device configured to process the horse heart rate information from the transmitter and display the processed horse heart rate information on a screen of the wearable electronic device.

9. The system of claim 8, wherein the one or more flaps comprise two opposing flaps.

10. The system of claim 9, wherein the two opposing flaps comprise hook and loop fastener material, such that the two opposing flaps are releasably securable to each other when wrapped around the girth portion of the saddle.

11. The system of claim 8, the wearable electronic device further comprising a heart rate monitoring sensor configured to detect rider heart rate information; wherein the computer application of the wearable electronic device is further configured to process the rider heart rate information and display the processed rider heart rate information on the screen of the wearable electronic device with the processed horse heart rate information.

12. The system of claim 8, the at least two electrodes including two electrodes having significantly different sizes, wherein the HR monitoring strap is configured such that a larger of the two electrodes is positioned higher than a smaller of the two electrodes, the smaller of the two electrodes being positioned behind a left elbow of the horse.

13. The system of claim 8, wherein the transmitter is electrically connected to each of the at least two electrodes by a respective conductive member.

14. The system of claim 8, wherein the HR monitoring strap is approximately 500 millimeters in length.

15. A method for monitoring a heart rate of a horse over the course of a plurality of rides comprising:
installing a noncircumferential horse heart rate monitoring (HRM) strap on a horse by:
placing a saddle on the horse;
after placing the saddle on the horse, disposing the horse HRM strap on an exterior surface of the horse such that an upper end of the horse HRM strap is under a saddle pad of the saddle and a lower end of the horse HRM strap is disposed behind a left elbow of the horse, and the horse HRM strap is sandwiched between a body of the horse and an underside of a girth portion of the saddle; and
securing the horse HRM strap in place by fastening one or more flaps, each extending from a respective lateral side of the horse HRM strap, around an outer side of the girth portion of the saddle; and
using a heart rate monitoring system to measure a heart rate of the horse using the noncircumferential horse HRM strap during each ride of a plurality of rides;
wherein the heart rate monitoring system is configured to determine and display characteristics of each of the plurality of rides on a screen display of an electronic device, and the characteristics of each of the plurality of rides include the heart rate of the horse.

16. The method of claim 15, further comprising:
automatically measuring a heart rate of a rider during each ride of the plurality of rides; and
displaying rider heart rate information, in real time during each ride, on the display of the electronic device.

17. The method of claim 16, wherein the electronic device comprises a wearable electronic device wearable by the rider, and wherein automatically measuring the heart rate of the rider is performed using the wearable electronic device.

18. The method of claim 15, wherein displaying characteristics of each of the plurality of rides on the display of the electronic device comprises displaying a zone corresponding to the heart rate of the horse.

19. The method of claim 15, further comprising establishing a resting heart rate of the horse by:
placing a surcingle on the horse;
placing the horse HRM strap on the horse under the surcingle such that the lower end of the horse HRM strap is behind the left elbow of the horse;
fastening the surcingle while the horse HRM strap remains positioned between the surcingle and the horse, with the horse HRM strap generally oriented in a direction defined by the surcingle; and
monitoring the heart rate of the horse while the horse is resting.

20. The method of claim 15, wherein the characteristics of each ride further include one or more characteristics selected from a list consisting of a duration, an intensity, a style, and a location.

21. An equine performance tracking and monitoring system comprising:
an elongate heart rate (HR) monitoring strap having a first electrode at a first end portion and a second electrode at a second end portion, the first and second electrodes being electrically coupled to a transmitter;

one or more flaps, each extending outward from a long edge of the elongate HR monitoring strap, wherein the HR monitoring strap is configured to attach to a horse by sandwiching the strap between a body of the horse and a girth portion of a saddle on the horse with the one or more flaps releasably fastened around the girth portion of the saddle, such that the heart rate monitoring strap is against the body of the horse and extends only partially around the body of the horse, and wherein the first and second electrodes monitor a heart rate of the horse; and a wearable electronic device, wearable by a rider of the horse, having a display screen and configured to receive heart rate signals from the transmitter of the HR monitoring strap, the wearable electronic device further comprising a heart rate sensor configured to detect a heart rate of the rider and a memory configured to store synchronized data corresponding to the heart rate of the rider and the heart rate of the horse;

wherein a processor of the wearable electronic device is configured to execute a set of stored instructions to determine a heart rate zone, selected from a plurality of defined heart rate zones, corresponding to a currently measured heart rate of the horse, and to cause the display screen to present, in real time, an indicator corresponding to the determined heart rate zone.

* * * * *